(12) United States Patent
Garcia et al.

(10) Patent No.: US 11,389,142 B2
(45) Date of Patent: *Jul. 19, 2022

(54) END EFFECTOR COUPLER FOR SURGICAL ARM

(71) Applicant: Zimmer Biomet CMF and Thoracic, LLC, Jacksonville, FL (US)

(72) Inventors: Saddy Garcia, St. Augustine, FL (US); Jeffrey Schlosser, Menlo Park, CA (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 170 days.

This patent is subject to a terminal disclaimer.

(21) Appl. No.: 16/879,500

(22) Filed: May 20, 2020

(65) Prior Publication Data

US 2020/0281576 A1 Sep. 10, 2020

Related U.S. Application Data

(63) Continuation of application No. 15/918,531, filed on Mar. 12, 2018, now Pat. No. 10,687,792.

(51) Int. Cl.
*A61B 17/00* (2006.01)
*A61B 90/50* (2016.01)
*A61B 90/57* (2016.01)
*A61B 17/28* (2006.01)
*A61B 17/02* (2006.01)

(52) U.S. Cl.
CPC ............. *A61B 17/00* (2013.01); *A61B 17/02* (2013.01); *A61B 17/28* (2013.01); *A61B 90/50* (2016.02); *A61B 2017/00477* (2013.01); *A61B 2017/00482* (2013.01); *A61B 2090/571* (2016.02)

(58) Field of Classification Search
CPC ................................ A61B 17/00; A61B 90/50
See application file for complete search history.

(56) References Cited

U.S. PATENT DOCUMENTS

| 2,752,116 A | 6/1956 | Minnis |
| 3,910,538 A | 10/1975 | Baitella |
| 4,402,481 A | 9/1983 | Sasaki |

(Continued)

FOREIGN PATENT DOCUMENTS

| CN | 107614817 A | 1/2018 |
| DE | 10201510481 A1 | 9/2016 |

(Continued)

OTHER PUBLICATIONS

US 10,792,124 B2, 10/2020, Billard et al. (withdrawn)

(Continued)

*Primary Examiner* — Tessa M Matthews
(74) *Attorney, Agent, or Firm* — Schwegman Lundberg & Woessner, P.A.

(57) ABSTRACT

An end effector coupler for a surgical arm can include a body, a proximal coupler, and a tool lock. The tool lock can releasably retain a tool stem to the end effector coupler. The tool lock can include a keyed opening, a pin bore, a pin disposed in the bin bore, a biasing element located in the pin bore, and a pin release including an actuator, the pin release operable to retract the pin into to the body to disengage the pin from the tool stem allowing release of the tool stem from the keyed opening.

20 Claims, 11 Drawing Sheets

(56) References Cited

U.S. PATENT DOCUMENTS

| | | | |
|---|---|---|---|
| 4,514,117 A | | 4/1985 | Scott |
| 5,348,259 A | * | 9/1994 | Blanco .................. A61B 17/115 227/19 |
| 5,779,209 A | | 7/1998 | Rello |
| 5,824,085 A | | 10/1998 | Sahay et al. |
| 5,899,425 A | * | 5/1999 | Corey Jr. .............. A61B 17/02 248/276.1 |
| 6,467,362 B2 | | 10/2002 | Erikson |
| 6,575,653 B1 | | 6/2003 | Kräuter |
| 6,860,877 B1 | | 3/2005 | Sanchez et al. |
| 7,182,731 B2 | * | 2/2007 | Nguyen ............. A61B 17/0206 600/229 |
| 7,611,378 B1 | | 11/2009 | Brekosky et al. |
| 9,592,096 B2 | | 3/2017 | Maillet et al. |
| D878,585 S | | 3/2020 | Garcia |
| 10,687,792 B2 | | 6/2020 | Garcia et al. |
| 10,687,915 B2 | | 6/2020 | Schlosser et al. |
| 10,772,704 B2 | | 9/2020 | Garcia et al. |
| 10,786,264 B2 | * | 9/2020 | Chegini ............. A61B 17/1671 |
| 10,835,345 B2 | | 11/2020 | Billard et al. |
| D910,848 S | | 2/2021 | Garcia |
| 10,987,175 B2 | | 4/2021 | Britton et al. |
| 11,179,222 B2 | | 11/2021 | Schlosser et al. |
| 2002/0017857 A1 | | 2/2002 | Hashimoto et al. |
| 2002/0074472 A1 | | 6/2002 | Gaida et al. |
| 2002/0117857 A1 | | 8/2002 | Eckstein |
| 2002/0177857 A1 | | 11/2002 | Otsuka et al. |
| 2002/0188293 A1 | | 12/2002 | Manzo |
| 2004/0172012 A1 | | 9/2004 | Otsuka et al. |
| 2008/0142658 A1 | | 6/2008 | Jurja |
| 2008/0164395 A1 | | 7/2008 | Chang et al. |
| 2010/0020002 A1 | | 1/2010 | Van Woudenberg et al. |
| 2010/0200002 A1 | | 8/2010 | Orban, III et al. |
| 2011/0290855 A1 | | 12/2011 | Moore et al. |
| 2011/0315843 A1 | | 12/2011 | Hung |
| 2012/0182134 A1 | | 7/2012 | Doyle |
| 2012/0265240 A1 | | 10/2012 | Ganske et al. |
| 2013/0187022 A1 | | 7/2013 | Duportal et al. |
| 2013/0292522 A1 | | 11/2013 | Sears |
| 2013/0299658 A1 | | 11/2013 | Hung |
| 2014/0343572 A1 | | 11/2014 | Windolf et al. |
| 2014/0379038 A1 | | 12/2014 | Dogramadzi et al. |
| 2015/0032215 A1 | | 1/2015 | Slamin et al. |
| 2015/0100066 A1 | | 4/2015 | Kostrzewski et al. |
| 2016/0081753 A1 | | 3/2016 | Kostrzewski |
| 2016/0151120 A1 | | 6/2016 | Kostrzewski et al. |
| 2016/0270780 A1 | | 9/2016 | Hall et al. |
| 2017/0034021 A1 | | 11/2017 | Chuang |
| 2017/0340389 A1 | | 11/2017 | Otto et al. |
| 2017/0360521 A1 | | 12/2017 | Johnson |
| 2018/0116758 A1 | | 5/2018 | Schlosser et al. |
| 2018/0256217 A1 | | 9/2018 | Dekel et al. |
| 2018/0360544 A1 | | 12/2018 | Vanheule et al. |
| 2019/0167356 A1 | | 6/2019 | Britton et al. |
| 2019/0274665 A1 | | 9/2019 | Garcia |
| 2019/0274777 A1 | | 9/2019 | Garcia et al. |
| 2019/0274778 A1 | | 9/2019 | Billard et al. |
| 2019/0274780 A1 | | 9/2019 | Nowatschin et al. |
| 2020/0352676 A1 | | 11/2020 | Schlosser et al. |
| 2021/0236211 A1 | | 8/2021 | Britton et al. |

FOREIGN PATENT DOCUMENTS

| | | | |
|---|---|---|---|
| EP | 2777539 A2 | 9/2014 | |
| EP | 2143372 B1 | 12/2014 | |
| EP | 3274521 A1 | 1/2018 | |
| JP | S57144399 A | 9/1982 | |
| JP | 63280911 A | 11/1988 | |
| JP | S63280911 A | 11/1988 | |
| JP | 2001187064 A | 7/2001 | |
| JP | 2018509273 A | 4/2018 | |
| JP | 2021062232 A | 4/2021 | |
| WO | WO-9639944 A1 | 12/1996 | |
| WO | WO-2014108898 A1 | 7/2014 | |
| WO | WO-2016160272 A1 | 10/2016 | |
| WO | WO-2017017443 A1 | 2/2017 | |
| WO | WO-2017151887 A1 | 9/2017 | |
| WO | WO-2019177567 A1 | 9/2019 | |
| WO | WO-2019177569 A1 | 9/2019 | |
| WO | WO-2019177570 A1 | 9/2019 | |

OTHER PUBLICATIONS

"U.S. Appl. No. 15/918,531, Corrected Notice of Allowability dated May 20, 2020", 2 pgs.

"U.S. Appl. No. 15/919,161, Notice of Allowance dated Jun. 4, 2020", 9 pgs.

"U.S. Appl. No. 16/210,787, Response filed Jun. 15, 2020 to Restriction Requirement dated Apr. 16, 2020", 6 pgs.

"3840 Series Holder", Fisso—Rail-mounted instrument holding arm / articulated, [Online]. [Accessed Oct. 16, 2017]. Retrieved from the Internet: <URL: http://www.medicalexpo.com/prod/fisso/product-67723-681104.html>, 3 pgs.

"3D-Arm™", Elekta—Minimally invasive surgery instrument holding arm, [Online]. [Accessed Oct. 16, 2017]. Retrieved from the Internet: <URL: http://www.medicalexpo.com/prod/elekta/product-70692-509376.html>, 8 pgs.

"ALLY Uterine Positioning System", Cooper Surgical, [Online]. [Accessed Oct. 16, 2017]. Retrieved from the Internet: <URL: https://www.coopersurgical.com/Products/Detail/ALLY-Uterine-Positioning-System>, 2 pgs.

"Anatomical Shoulder Fracture System", Zimmer Surgical Technique, 97-4223-003-00 Rev. 1, (2005), 24 pgs.

"Anatomical Shoulder Glenoid", Zimmer Surgical Technique, (2014), 12 pgs.

"U.S. Appl. No. 15/560,894, Final Office Action dated Nov. 29, 2019", 8 pgs.

"U.S. Appl. No. 15/560,894, Non Final Office Action dated May 16, 2019", 9 pgs.

"U.S. Appl. No. 15/560,894, Notice of Allowance dated Feb. 13, 2020", 8 pgs.

"U.S. Appl. No. 15/560,894, Preliminary Amendment filed Sep. 22, 2017", 7 pgs.

"U.S. Appl. No. 15/560,894, Response filed Jan. 28, 2020 to Final Office Action dated Nov. 29, 2019", 7 pgs.

"U.S. Appl. No. 15/560,894, Response filed Mar. 21, 2019 to Restriction Requirement dated Dec. 31, 2018", 9 pgs.

"U.S. Appl. No. 15/560,894, Response filed Aug. 16, 2019 to Non Final Office Action dated May 16, 2019", 11 pgs.

"U.S. Appl. No. 15/560,894, Restriction Requirement dated Dec. 31, 2018", 7 pgs.

"U.S. Appl. No. 15/560,894, Supplemental Preliminary Amendment filed Sep. 29, 2017", 7 pgs.

"U.S. Appl. No. 15/918,531, Non Final Office Action dated Sep. 26, 2019", 12 pgs.

"U.S. Appl. No. 15/918,531, Notice of Allowance dated Feb. 19, 2020", 11 pgs.

"U.S. Appl. No. 15/918,531, Response filed Dec. 26, 2019 to Non Final Office Action dated Sep. 26, 2019", 12 pgs.

"U.S. Appl. No. 15/919,150, Non Final Office Action dated Jan. 13, 2020", 10 pgs.

"U.S. Appl. No. 15/919,150, Notice of Allowance dated May 12, 2020", 5 pgs.

"U.S. Appl. No. 15/919,150, Response filed Apr. 10, 2020 to Non Final Office Action dated Jan. 13, 2020", 11 pgs.

"U.S. Appl. No. 15/919,161, Final Office Action dated Feb. 19, 2020", 7 pgs.

"U.S. Appl. No. 15/919,161, Non Final Office Action dated Sep. 26, 2019", 18 pgs.

"U.S. Appl. No. 15/919,161, Response filed May 18, 2020 to Final Office Action dated Feb. 19, 2020", 10 pgs.

"U.S. Appl. No. 15/919,161, Response filed Dec. 26, 2019 to Non Final Office Action dated Sep. 26, 2019", 13 pgs.

"U.S. Appl. No. 16/210,787, Restriction Requirement dated Apr. 16, 2020", 5 pgs.

"U.S. Appl. No. 29/640,121, Corrected Notice of Allowability dated Jan. 21, 2020", 4 pgs.

(56) References Cited

OTHER PUBLICATIONS

"U.S. Appl. No. 29/640,121, Notice of Allowance dated Nov. 5, 2019", 8 pgs.

"ASSISTO Arm System", Geomed GMBH, [Online]. [Accessed Oct. 16, 2017]. Retrieved from the Internet: <URL: http://www.geomed.de/index.php?id=65&L=1>, 1 pg.

"Atlas™ Flex Arm System", Axcess Surgical, [Online]. [Accessed Oct. 16, 2017]. Retrieved from the Internet: <URL: http://www.axcesssurgical.com/axcess-surgical-innovations-products/atlas-flex-arm-system/>, 5 pgs.

"Atlas™ Rigid Arm System", Axcess Surgical, [Online]. [Accessed Oct. 16, 2017]. Retrieved from the Internet: <URL: http://www.axcesssurgical.com/axcess-surgical-innovations-products/atlas-rigid-arm-system/>, 6 pgs.

"Australian Application Serial No. 2016243292, First Examination Report dated Apr. 7, 2020", 4 pgs.

"Bookler® Strong Arm™ Holder", Mediflex, [Online]. [Accessed Nov. 2, 2017]. Retrieved from the Internet: <URL: http://www.mediflex.com/product/bookler-strongarm-holder-and-positioner-set-12-30cm-post/>, (2015), 4 pgs.

"Canadian Application Serial No. 3,002,354, Office Action dated Apr. 27, 2020", 3 pgs.

"Canadian Application Serial No. 3,002,354, Office Action dated Jul. 4, 2019", 4 pgs.

"Canadian Application Serial No. 3,002,354, Response filed Dec. 20, 2019 to Office Action dated Jul. 4, 2019", 14 pgs.

"Chinese Application Serial No. 201680027778.9, Office Action dated Feb. 6, 2020", with English translation, 6 pages.

"Chinese Application Serial No. 201680027778.9, Office Action dated Jul. 12, 2019", w/English Translation, 20 pgs.

"Chinese Application Serial No. 201680027778.9, Response filed Mar. 19, 2020 to Office Action dated Feb. 6, 2020", with English claims, 8 pages.

"Chinese Application Serial No. 201680027778.9, Response filed Oct. 31, 2019 to Office Action dated Jul. 12, 2019", (w/English Claims), 15 pgs.

"Comprehensive Segmental Revision System, Proximal Humeral Reconstruction, Distal Humeral Reconstruction, Total Humeral Reconstruction", Zimmer Biomet Surgical Technique, 0097.1-US-en-REV0416, (2016), 68 pgs.

"EndoArm", Olympus, [Online]. [Accessed Nov. 2, 2017]. Retrieved from the Internet: <URL: https://www.olympus.co.jp/jp/news/2003b/nr030925endoj.html>, (Sep. 25, 2003), 4 pgs.

"EndoBoy", LUT—Pneumatic Arm, Grecco, 8 pgs.

"EndoCrane", Karl Storz—LEROY Retractors for Laparoscopic Colorectal Surgery, [Online]. [Accessed Oct. 16, 2017]. Retrieved from the Internet: <URL: https://www.karlstorz.com/cps/rde/xbcr/karlstorz_assets/ASSETS/2193800.pdf>, 16 pgs.

"European Application Serial No. 16773696.6, Extended European Search Report dated Nov. 19, 2018", 8 pgs.

"European Application Serial No. 16773696.6, Response filed Jun. 4, 2018 to Office Action dated Nov. 22, 2018".

"European Application Serial No. 16773696.6, Response filed Jun. 17, 2019 to Extended European Search Report dated Nov. 19, 2018", 18 pgs.

"European Application Serial No. 18210813.4, Extended European Search Report dated Apr. 12, 2019", 7 pgs.

"Genzyme Remote Surgical Retractor Arm Hands Free Pneumatic System", Renix International/Alibaba.com Copyright 1999-2017, [Online]. [Accessed Nov. 2, 2017]. Retrieved from the Internet: <URL: http://renix.trustpass.alibaba.com/product/50001078652-219532304/Genzyme_Remote_Surgical_Retractor_Arm_Hands_Free_Pneumatic_System.html>, 2 pgs.

"Helping Hand", Fraunhofer IPA—The helping hand in the operation room Research News, [Online]. [Accessed Oct. 16, 2017]. Retrieved from the Internet: <URL: https://www.fraunhofer.de/en/press/research-news/2015/november/helping-hand-in-the-operation-room.html>, (Nov. 2015), 2 pgs.

"International Application Serial No. PCT/US2016/021076, International Preliminary Report on Patentability dated Oct. 12, 2017", 11 pgs.

"International Application Serial No. PCT/US2016/021076, International Search Report dated Aug. 11, 2016", 4 pgs.

"International Application Serial No. PCT/US2016/021076, Invitation to Pay Add'l Fees and Partial Search Report dated May 25, 2016", 2 pgs.

"International Application Serial No. PCT/US2016/021076, Written Opinion dated Aug. 11, 2016", 8 pgs.

"International Application Serial No. PCT/US2018/021988, International Search Report dated Dec. 20, 2018", 4 pgs.

"International Application Serial No. PCT/US2018/021988, Written Opinion dated Dec. 20, 2018", 6 pgs.

"International Application Serial No. PCT/US2018/022004, International Search Report dated Feb. 14, 2019", 8 pgs.

"International Application Serial No. PCT/US2018/022004, Invitation to Pay Additional Fees dated Dec. 19, 2018", 15 pgs.

"International Application Serial No. PCT/US2018/022004, Written Opinion dated Feb. 14, 2019", 14 pgs.

"International Application Serial No. PCT/US2018/022006, International Search Report dated Feb. 8, 2019", 8 pgs.

"International Application Serial No. PCT/US2018/022006, Invitation to Pay Additional Fees dated Dec. 12, 2018", 16 pgs.

"International Application Serial No. PCT/US2018/022006, Written Opinion dated Feb. 8, 2019", 15 pgs.

"IronIntern", Automated Medical, [Online]. [Accessed Oct. 16, 2017]. Retrieved from the Internet: <URL: http://ironintern.com/iron-intern%E2%84%A2>, 1 pg.

"Japanese Application Serial No. 2018-501138, Notification of Reasons for Refusal dated Nov. 5, 2019", (w/English Translation), 15 pgs.

"Japanese Application Serial No. 2018-501138, Response filed Apr. 22, 2020 to Notification of Reasons for Refusal dated Nov. 5, 2019", (W/ English Translation of Claims), 15 pgs.

"Jarit Endoscope Holder", Integra, [Online]. [Accessed Oct. 16, 2017]. Retrieved from: <URL: https://www.integralife.com/endoscope-instrument-holder-set/product/surgical-instruments-hospitals-surgery-centers-tissue-banks-jarit-laparoscopic-endoscopes-endoscope-instrument-holder-set>, 18 pgs.

"M-Trac", Aesculap / B Braun, [Online]. [Accessed—Oct. 16, 2017]. Retrieved from the Internet: <URL: https://www.bbraun.com/en/products/b/m-trac.html>, 2 pgs.

"Martin's Arm", Hayden Medical (& others), [Online]. [Accessed Oct. 16, 2017]. Retrieved from the Internet: <URL: http://haydenmedical.com/surgical-retractors-martins-arm-retractors/>, 2 pgs.

"Mechanical Arm—Mod. 8470", Ansabere Surgical, [Online]. [Accessed Oct. 16, 2017]. Retrieved from the Internet: <URL: http://www.ansaberesurgical.com/en/productos/brazos-mecanicos/brazo-mecanico-mod-8470/>, 5 pgs.

"Phantom ML", TeDan Surgical Innovations, [Online]. [Accessed Nov. 14, 2017]. Retrieved from the Internet: <URL: http://www.tedansurgical.com/spine/articulating-arms/>, 2 pgs.

"Point Setter", Mitaka Kohki Co., Ltd. Operating / User's Manual Model: PSMS2, (Feb. 14, 2010), 28 pgs.

"PositionOR", Surgical Concept Designs, [Online]. [Acessed Nov. 14, 2017]. Retrieved from the Internet: <URL: http://surgical-concepts.com/products/PositionOR/>, 1 pg.

"Postioning Arm", Civco—Laparostat™ Kit, [Online]. [Accessed Oct. 16, 2017]. Retrieved from the Internet: <URL: http://www.civco.com/mmi/resources/ifu/043687.pdf>, 16 pgs.

"SaphLITE | RadLITE", Teleflex Medical, [Online]. [Accessed Nov. 14, 2017]. Retrieved from the Internet: <URL: https://www.teleflex.com/en/usa/prod_saphlite-radlite.php>, 1 pg.

"Saphlite/Saphlift", Genzyme Surgical Products (Jan. 7, 1999), [Online]. [Accessed Oct. 16, 2017]. Retrieved from the Internet: <URL: https://www.accessdata.fda.gov/cdrh_docs/pdf/K990062.pdf>, 5 pgs.

"Speed-Tract", Integra—Table Mounted Speed—Tract Retractor System, [Online]. [Accessedd Oct. 16, 2017]. Retrieved from the Internet: <URL: http://occ.integralife.com/products%2Fpdfs%

(56) References Cited

OTHER PUBLICATIONS

2Fintegra%20table%20mounted%20speed-tract%20retractor%20system%20brochure.pdf>, 6 pgs.

"Spider2 Limb Positioner", Smith & Nephew, [Online]. [Accessed Oct. 14, 2017]. Retrieved from the Internet: <URL: http://www.smith-nephew.com/new-zealand/advanced-surgical-devices/key-products/sports-medicine/spider2-limb-positioner-for-shoulder--hip--knee--/>, 2 pgs.

"Spine Endoscope & Endoscope Holder", Maxer, [Online]. [Accessed Nov. 2, 2017]. Retrieved from the Internet: <URL: http://www.maxerendoscopy.com/index.php?option=com_content&view=article&id=190:spine-endoscope-endoscope-holder&catid=81:spine-endoscopy&Itemid=858>, (2013).

"SurgiAssist Camera Holder", SurgiToolsMIS, [Online]. [Accessed Oct. 14, 2017]. Retrieved from the Internet: <URL: https://www.surgitools.com/surgiassist-camera-holder.html>, 4 pgs.

"Synaptive BrightMatter Drive Robotic Surgical Video Arm System", Synaptive, [Online]. [Accessed Nov. 14, 2017]. Retrieved from the Internet: <URL: https://www.medgadget.com/2016/05/synaptive-brightmatter-drive-robotic-surgical-videoarm-system.html>, 3 pgs.

"TEE Transducer Holder", Civco, [Online]. [Accessed Oct. 16, 2017]. Retrieved from the Internet: <URL: http://www.civco.com/mmi/resources/product-support/TEE-Holder-Brochure_2008P-2339-Rev-2_low-res-8l9rv5.pdf>, 8 pgs.

"The Freehand System", Freehand—V1.2, [Online]. [Acessed Oct. 16, 2017]. Retrieved from the Internet: <URL: http://freehandsurgeon.com/Products/Detail?id=2>, 3 pgs.

"TIREX® Retractor System", Orion Surgical, [Online]. [Accessed Nov. 2, 2017]. Retrieved from the Internet: <URL: http://www.orion-surgical.com/english/tirex-retractor-system/components-of-the-tirex.html>, (2017), 2 pgs.

"TRIMANO 3D Support Arm", Maquet, [Online]. [Accessed Oct. 16, 2017]. Retrieved from the Internet: <URL: https://www.maquet.com/int/products/trimano-3d-support-arm/>, 3 pgs.

"UniARM Surgical Support System", Mitaka Kohki Co., Ltd. Operating / User Manual Version 1.1, [Online]. [Accessed Nov. 2, 2017]. Retrieved from the Internet: <URL: http://mitakausa.com/uniarm/>, (Mar. 20, 2009), 19 pgs.

"Unitrac Retraction & holding system for open & minimally invasive surgery", Aesculap Surgical Technologies—Surgical Instruments, (2010), 12 pgs.

"Unitrac® Pneumatic Holding Arm", Aesculap / B Braun, [Online]. [Accessed Oct. 16, 2017]. Retrieved from the Internet: <URL: https://www.bbraun.com/en/products/b/unitrac-pneumaticholdingarm.html>, 3 pgs.

"Vertek Articulating Arm", Medtronic—Copyright 2013, [Online]. [Accessed Nov. 2, 2017]. Retrieved from the internet: <URL: http://global.medtronic.com/xg-en/healthcare-professionals/products/neurological/surgical-navigation-imaging/neurosurgery-imaging-surgical-navigation/surgical-procedures.html>, 2 pgs.

"VIKY", Endocontrol Medical, [Online]. [Accessed 2014]. Retrieved from the Internet: <URL: http://www.endocontrol-medical.com/en/viky-en/>, 5 pgs.

"Wingman Scope Holder", Stryker, [Online], [Accessed Nov. 14, 2017], Retrieved from the Internet: <URL: http://www.stryker.com/cn/products/OREquipmentTelemedicine/EndoscopicSurgeryEquipment/Laparoscopy/Accessories/ScopeHolder/index.htm#>, 3 pgs.

"U.S. Appl. No. 15/919,150, Supplemental Notice of Allowability dated Jul. 6, 2020", 2 pgs.

"U.S. Appl. No. 15/919,150, Supplemental Notice of Allowability dated Jul. 29, 2020", 2 pgs.

"U.S. Appl. No. 15/919,161, Corrected Notice of Allowability dated Jul. 29, 2020", 2 pgs.

"U.S. Appl. No. 15/919,161, Corrected Notice of Allowability dated Aug. 26, 2020", 4 pgs.

"U.S. Appl. No. 15/919,161, Corrected Notice of Allowability dated Oct. 15, 2020", 2 pgs.

"U.S. Appl. No. 16/210,787, Non Final Office Action dated Sep. 15, 2020", 7 pgs.

"U.S. Appl. No. 16/210,787, Notice of Allowance dated Jan. 4, 2021", 8 pgs.

"U.S. Appl. No. 16/210,787, Response filed Dec. 9, 2020 to Non Final Office Action dated Sep. 15, 2020", 8 pgs.

"U.S. Appl. No. 16/877,023, Corrected Notice of Allowability dated Aug. 16, 2021", 2 pgs.

"U.S. Appl. No. 16/877,023, Ex Parte Quayle Action mailed Apr. 29, 2021", 7 pgs.

"U.S. Appl. No. 16/877,023, Notice of Allowance dated Jul. 22, 2021", 8 pgs.

"U.S. Appl. No. 16/877,023, Preliminary Amendment filed Jul. 31, 2020", 7 pgs.

"U.S. Appl. No. 16/877,023, Response filed Mar. 26, 2021 to Restriction Requirement dated Jan. 26, 2021", 10 pgs.

"U.S. Appl. No. 16/877,023, Response filed Jun. 24, 2021 to Ex Parte Quayle Action mailed Apr. 29, 2021", 4 pgs.

"U.S. Appl. No. 16/877,023, Restriction Requirement dated Jan. 26, 2021", 7 pgs.

"U.S. Appl. No. 29/721,682, Preliminary Amendment filed Jun. 24, 2021", 6 pgs.

"U.S. Appl. No. 29/721,682, Corrected Notice of Allowability dated Jan. 19, 2021", 3 pgs.

"U.S. Appl. No. 29/721,682, Examiner Interview Summary dated Sep. 17, 2020", 3 pgs.

"U.S. Appl. No. 29/721,682, Non Final Office Action dated Jun. 23, 2020", 7 pgs.

"U.S. Appl. No. 29/721,682, Notice of Allowance dated Oct. 5, 2020", 7 pgs.

"U.S. Appl. No. 29/721,682, Response filed Sep. 14, 2020 to Non Final Office Action dated Jun. 23, 2020", 9 pgs.

"Australian Application Serial No. 2016243292, Response filed Jun. 29, 2020 to First Examination Report dated Apr. 7, 2020", 30 pgs.

"Australian Application Serial No. 2016243292, Response filed Sep. 30, 2020 to Subsequent Examiners Report dated Jul. 30, 2020", 30 pgs.

"Australian Application Serial No. 2016243292, Subsequent Examiners Report dated Jul. 30, 2020", 5 pgs.

"Australian Application Serial No. 2016243292, Subsequent Examiners Report dated Oct. 14, 2020", 3 pgs.

"Canadian Application Serial No. 2,980,725, Office Action dated May 21, 2021", 6 pgs.

"Canadian Application Serial No. 2,980,725, Office Action dated Nov. 12, 2020", 4 pgs.

"Canadian Application Serial No. 2,980,725, Response filed Mar. 11, 2021 to Office Action dated Nov. 12, 2020", 17 pgs.

"Canadian Application Serial No. 2,980,725, Response filed Sep. 21, 2021 to Office Action dated May 21, 2021", 13 pages.

"Canadian Application Serial No. 3,002,354, Response filed Aug. 4, 2020 to Office Action dated Apr. 27, 2020", 18 pgs.

"Chinese Application Serial No. 201680027778.9, Office Action dated Jun. 12, 2020", with English translation, 18 pages.

"Chinese Application Serial No. 201680027778.9, Response filed Jul. 15, 2020 to Office Action dated Jun. 12, 2020", with English claims, 71 pages.

"European Application Serial No. 18713116.4, Response to Communication pursuant to Rules 161(1) and 162 EPC filed Apr. 29, 2021", 20 pgs.

"European Application Serial No. 18713548.8, Response to Communication pursuant to Rules 161(1) and 162 EPC filed Apr. 29, 2021", 21 pgs.

"European Application Serial No. 18713549.6, Response to Communication pursuant to Rules 161(1) and 162 EPC filed May 20, 2021", 23 pgs.

"International Application Serial No. PCT/US2018/021988, International Preliminary Report on Patentability dated Sep. 24, 2020", 8 pgs.

"International Application Serial No. PCT/US2018/022004, International Preliminary Report on Patentability dated Sep. 24, 2020", 14 pgs.

"International Application Serial No. PCT/US2018/022006, International Preliminary Report on Patentability dated Sep. 24, 2020", 15 pgs.

(56) References Cited

OTHER PUBLICATIONS

"Japanese Application Serial No. 2018-501138, Examiners Decision of Final Refusal dated May 11, 2021", (W/ English Translation), 6 pgs.
"Japanese Application Serial No. 2018-501138, Final Notification of Reasons for Refusal dated Sep. 29, 2020", (W/ English Translation), 5 pgs.
"Japanese Application Serial No. 2018-501138, Response filed Sep. 13, 2021 to Examiners Decision of Final Refusal dated May 11, 2021", with English claims, 18 pages.
"Japanese Application Serial No. 2018-501138, Response filed Dec. 28, 2020 to Final Notification of Reasons for Refusal dated Sep. 29, 2020", (W/ English Claims), 11 pgs.
"Korean Application Serial No. 10-2017-7030940, Notice of Preliminary Rejection dated Feb. 4, 2021", (W/ English Translation), 4 pgs.
"Korean Application Serial No. 10-2017-7030940, Notice of Preliminary Rejection dated Aug. 10, 2020", (W/ English Translation), 13 pgs.
"Korean Application Serial No. 10-2017-7030940, Response filed Mar. 31, 2021 to Notice of Preliminary Rejection dated Feb. 5, 2021", (W/English Translation), 11 pgs.
"Korean Application Serial No. 10-2017-7030940, Response filed Oct. 8, 2020 to Notice of Preliminary Rejection dated Aug. 10, 2020", (W/ English Translation), 34 pgs.
U.S. Appl. No. 17/218,455, filed Mar. 31, 2021, Robotic Shoulder Repair and Reconstruction.
U.S. Appl. No. 16/994,181, filed Aug. 14, 2020, End Effector Coupler for Surgical Arm.
U.S. Appl. No. 17/015,734, filed Sep. 9, 2020, End Effector Coupler for Surgical Arm.

\* cited by examiner

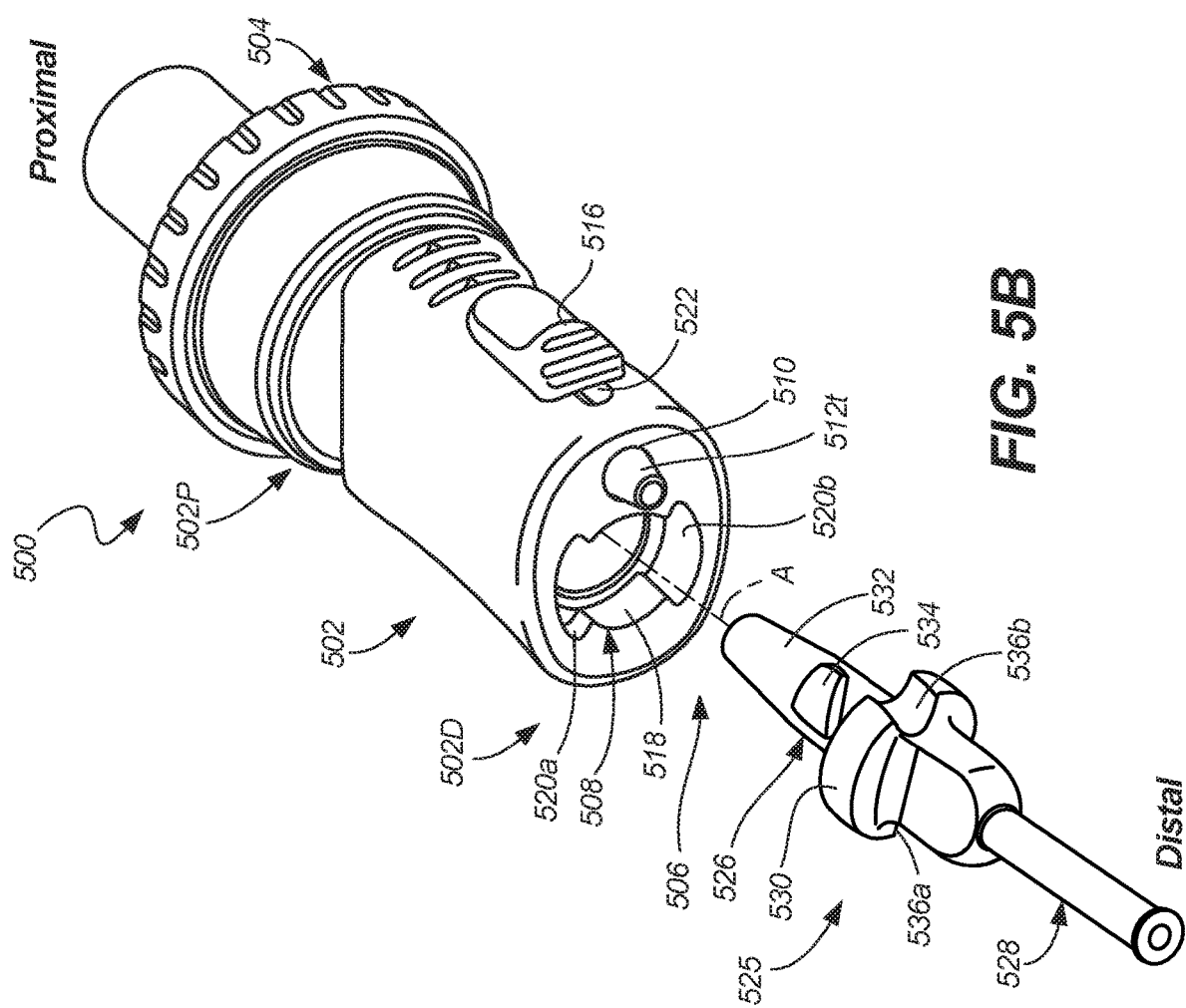
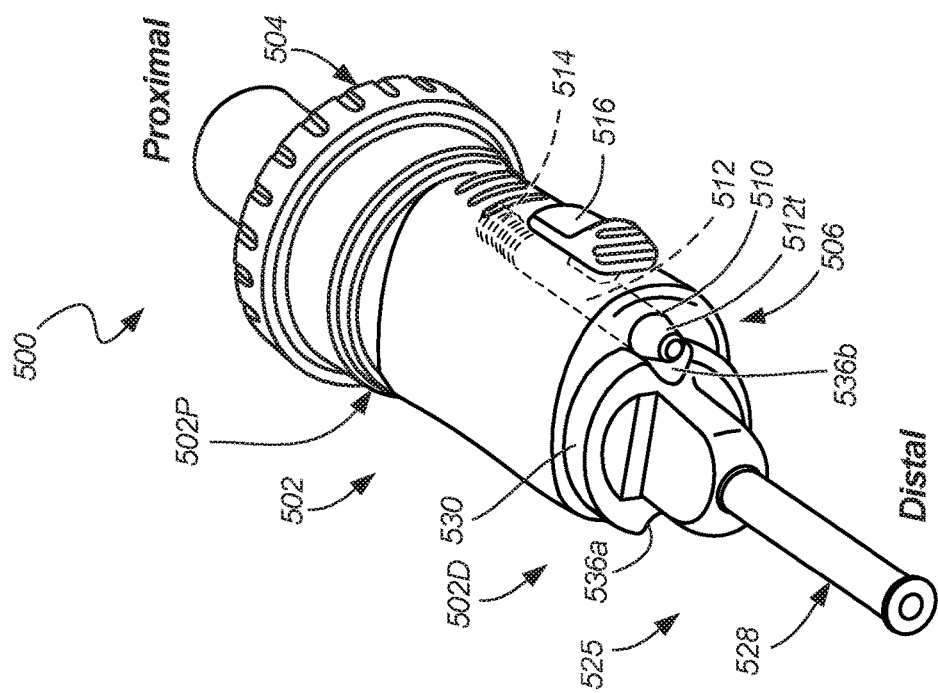
FIG. 5B
FIG. 5A

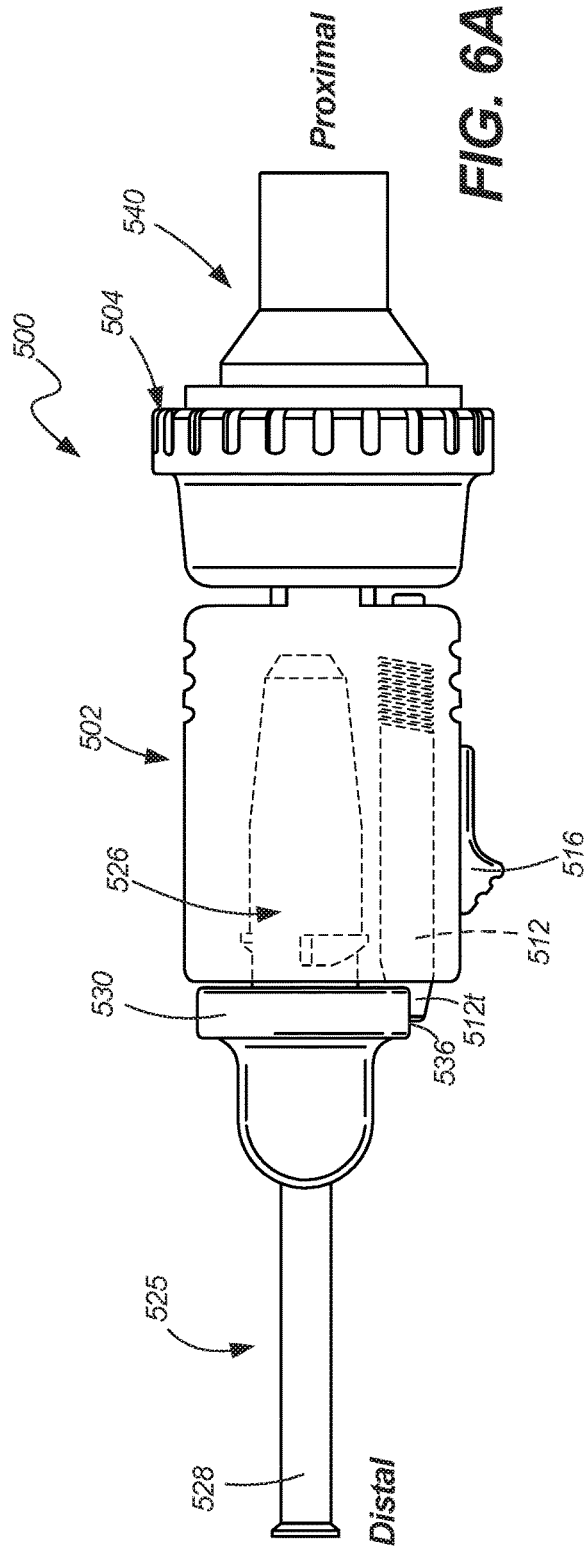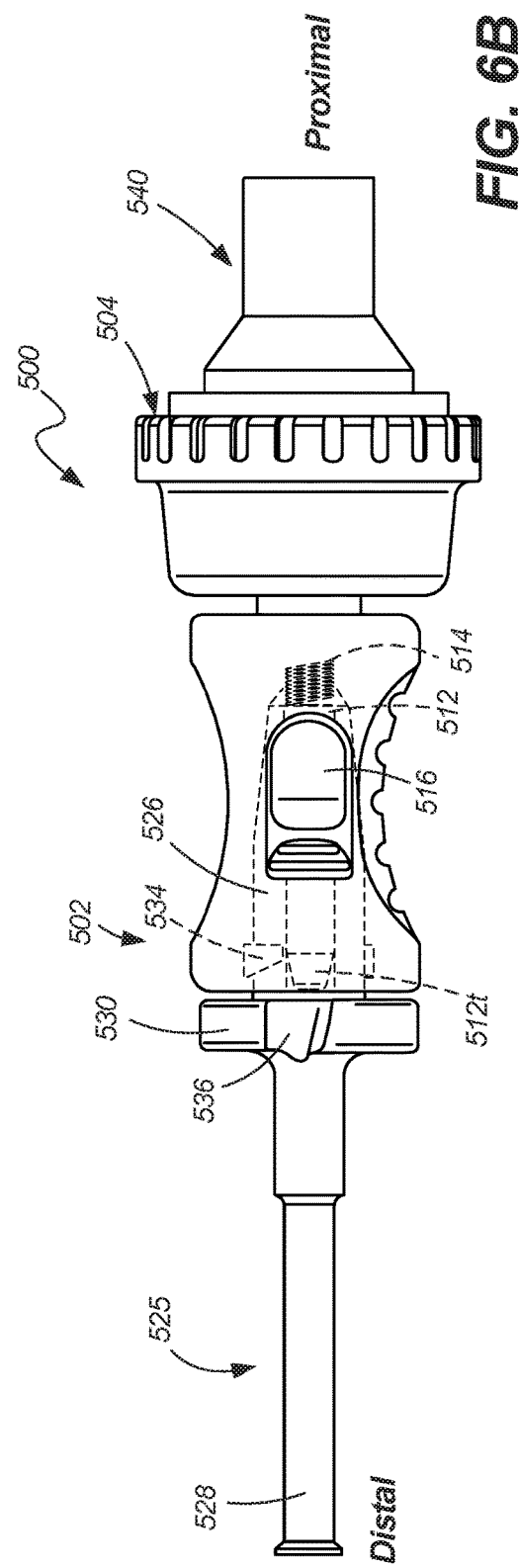

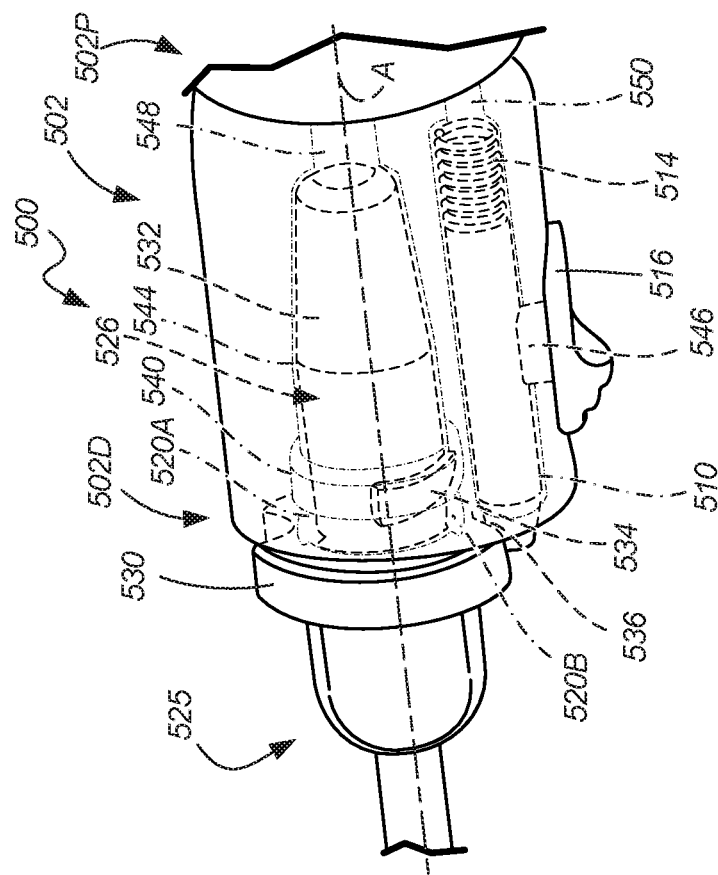
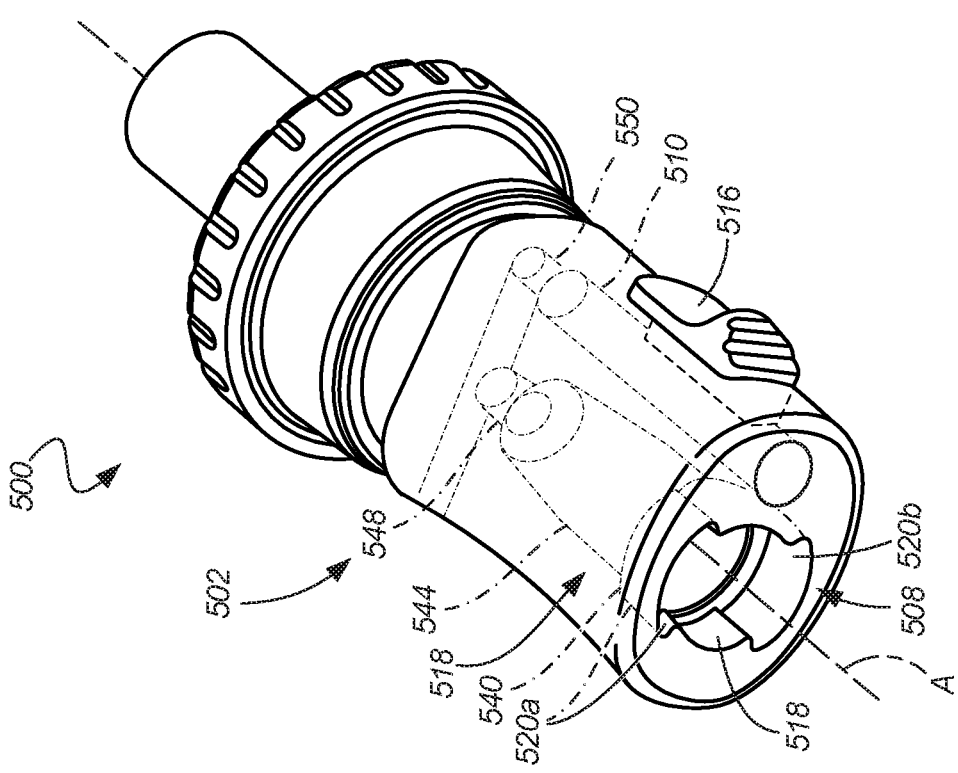
FIG. 7B
FIG. 7A

END EFFECTOR COUPLER FOR SURGICAL ARM

CROSS-REFERENCE TO RELATED PATENT DOCUMENTS

This application is a continuation of U.S. patent application Ser. No. 15/918,531, filed on Mar. 12, 2018, the benefit of priority of which is claimed hereby, and which is incorporated by reference herein in its entirety.

This patent application is also related to Jeffrey Schlosser et al., U.S. patent application Ser. No. 15/560,894 entitled "Rapidly Repositionable Powered Support Arm," filed on Sep. 22, 2017 which is hereby incorporated by reference herein in its entirety.

BACKGROUND

The present invention relates generally to apparatus and systems for supporting surgical and other tools. Some surgical procedures include use of a variety of tools. In some of these procedures, it is required that tools, such as a retractor, be maintained in a single position for an extended period of time, such as an hour or more. During this time, other tools can be used to perform other aspects of the surgery. Because it may be difficult or undesirable to manually hold a position of a tool for such lengths of time, mechanical and/or electromechanical arms can be used to hold the position of the tool while other aspects of the procedure are performed. Some arms can be adjustable such that a position of the arm can be adjusted before or during the procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5A illustrates an end effector coupler in a coupled condition, in accordance with at least one example of this disclosure.

FIG. 5B illustrates an end effector coupler in a decoupled condition, in accordance with at least one example of this disclosure.

FIG. 6A illustrates a top view of an end effector coupler, in accordance with at least one example of this disclosure.

FIG. 6B illustrates a side view of an end effector coupler, in accordance with at least one example of this disclosure.

FIG. 7A illustrates a perspective view of an end effector coupler, in accordance with at least one example of this disclosure.

FIG. 7B illustrates a bottom perspective view of an end effector coupler, in accordance with at least one example of this disclosure.

DETAILED DESCRIPTION

Figure 1:
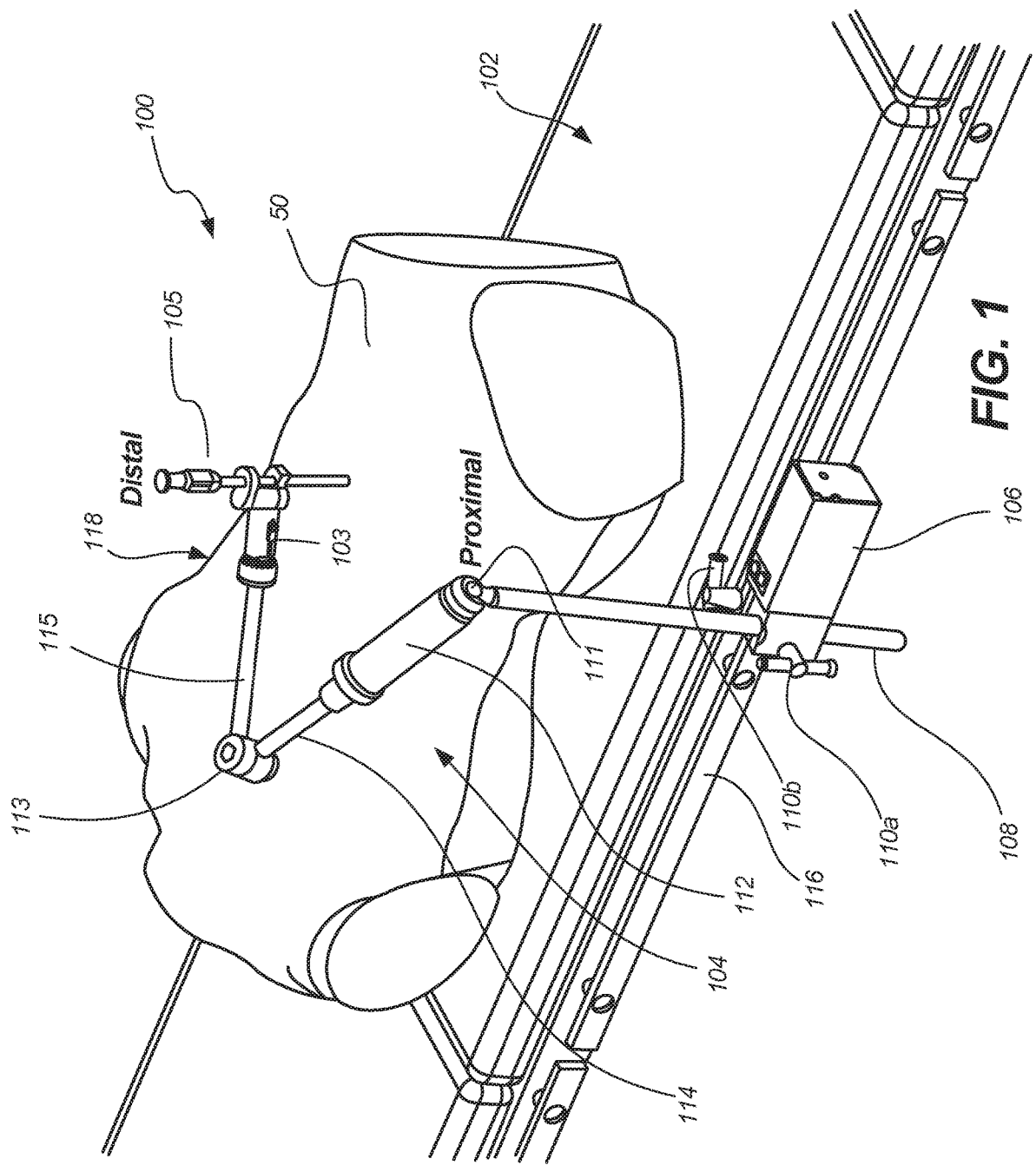
FIG. 1 illustrates a perspective view of a repositionable, lockable surgical arm system, in accordance with at least one example of this disclosure.

Some surgical procedures require a variety of tools. In some cases, it is desired to hold tools, such as a retractor, in a single position for an extended period of time, such as an hour or more. In these procedures, adjustable mechanical and/or electromechanical arms are often used to hold the position of the tool while other aspects of the procedure are performed. One type of arm sometimes employed is an arm that is manually articulable when unlocked and is prevented from being moved when locked. Because these arms are made for use with tools, there is a need for tools to secure to the arm. And, because a single procedure may require multiple tools and because the arms may be used for various procedures, there is a need for a method of quickly and easily securing a variety of tools to the arm.

This disclosure provides a solution to these issues through the use of an end effector coupler. The coupler can be releasably or fixedly secured to the arm and can include components allowing for tools to be released quickly and easily while providing a secure connection between the tool and the arm. More specifically, the end effector coupler can include a tool lock to secure a tool stem within the end effector coupler. As part of the locking engagement between the end effector and the tool, the tool stem and end effector body can interface in a taper-to-taper arrangement to reduce play or relative movement between the end effector coupler and the tool. Similarly, the end effector body and surgical arm can interface in a taper-to-taper arrangement to reduce play or relative movement between the end effector coupler and the surgical arm.

The end effector can also include a keyed opening and a counterbore coaxial with a central bore of the end effector. The tool stem can also include key bits configured to pass through keyways of the keyed opening to ensure alignment with the end effector, where the key bits also engage a surface between the counter bore and the proximal side of the keyed opening to as the tool is rotated; this can draw the stem completely within the end effector to secure the tool thereto.

Also, the locking mechanism can include a retractable pin (operable using an actuator), where the pin can extend from the bore to engage a flange of the stem. This locking engagement can prevent unwanted relative rotation of the tool and stem relative to the end effector coupler, helping to limit unwanted release of the tool from the end effector coupler. When it is desired to remove the tool, the pin can be retracted so that the tool and stem can be rotated for removal from the end effector coupler, allowing for quick release of tools from the end effector coupler. These and other features and benefits are discussed with reference to figures in further detail below.

As used herein, the terms "proximal" and "distal" should be given their generally understood anatomical interpretation. The term "proximal" refers to a direction generally toward the torso of a patient or base or handle of a tool, and "distal" refers to the opposite direction of proximal, i.e., away from the torso of a patient or toward the working end of the tool.

FIG. 1 illustrates a perspective view of repositionable, lockable surgical arm system 100, in accordance with at least one example of this disclosure. Lockable surgical arm system 100 can include table 102, arm 104, tool (or instrument) 105, and base unit 106. Table 102 can include rail 116. Base unit 106 can include pole 108 and manual clamp 110. Arm 104 can include proximal joint 111, actuator unit 112, distal joint 113, proximal arm 114, distal arm 115, and instrument holder 118. Also shown in FIG. 1 are orientation indicators Proximal and Distal (shown and discussed with respect to the adjustable arm).

Base unit 106, which can include power control circuit components for an electrically powered actuator (such as actuator 112), can be secured to rail 116 of surgical table 102 using, for example, a clamp. Manual clamp 110a of base unit 106 can be operated to tighten base unit 106 against railing 116 and manual clamp 110b can be operated for adjustment of pole 108 to set a height of arm 104 above surgical table 102.

Electric actuator unit 112 of arm 104 can be located near a proximal end of arm 104 and can be coupled to pole 108 at proximal joint 111. Electric actuator 112 can also be coupled to a proximal portion of proximal arm 114. Proximal arm 114 can be coupled to electric actuator 112 via a joint or as an actuatable part of actuator 112 in other examples. Distal arm 115 can be coupled to a distal portion of proximal arm 114 via distal joint 113. Instrument holder or end effector coupler 118 can connect instrument 105 to the distal end of arm 104. In some examples, a lock/unlock button can be provided on or near end effector coupler 118.

The arms of lockable surgical arm system 100 can comprise a serial linkage of arm segments joined by spherical and/or rotational joints. Each of joints 111 and 113 (and any other joints in other examples) can be pivotable and/or rotational joints allowing movement of connected components with one or more degrees of freedom. Joints 111 and 113 (and joints within actuator 112) can be locked and unlocked using base unit 106 and actuator 112, which can be an electric bilateral actuator. In some examples, the joints of the arm can be locked and unlocked with a fluid system.

While only proximal arm 114 and distal arm 115 are shown in FIG. 1, additional arm segments can be provided between actuator 112 and end effector coupler 118. Each additional arm segment may require one or more additional joints to form a repositionable, lockable support arm structure. Such additional arm segments can provide greater coverage and ability for the arm to be positioned with more degrees of freedom in the surgical field.

In operation of some examples, the lock/unlock button can be operable by a user to initiate power locking and unlocking of arm 104. When the lock/unlock button is not depressed arm 104 can be in a locked state where joints 111 and 113 are locked such that proximal arm 114 and distal arm 115 cannot move relative to each other or to table 102. When the lock/unlock button is pressed, actuator 112 can unlock joints 111 and 113 such that end effector coupler 118 can be positioned, as desired, and as guided by joints 111 and 113 and proximal arm 114 and distal arm 115. That is, end effector coupler 118 can be moved to a desired position relative to body 50 through movement paths limited by the freedom of arm 104 to position instrument 105 to a desired position relative to body 50.

FIG. 2A illustrates a perspective view of surgical arm system 200, in accordance with at least one example of this disclosure. FIG. 2B illustrates a perspective view of surgical arm 200, in accordance with at least one example of this disclosure. FIGS. 2A and 2B are discussed below concurrently.

Figure 2:
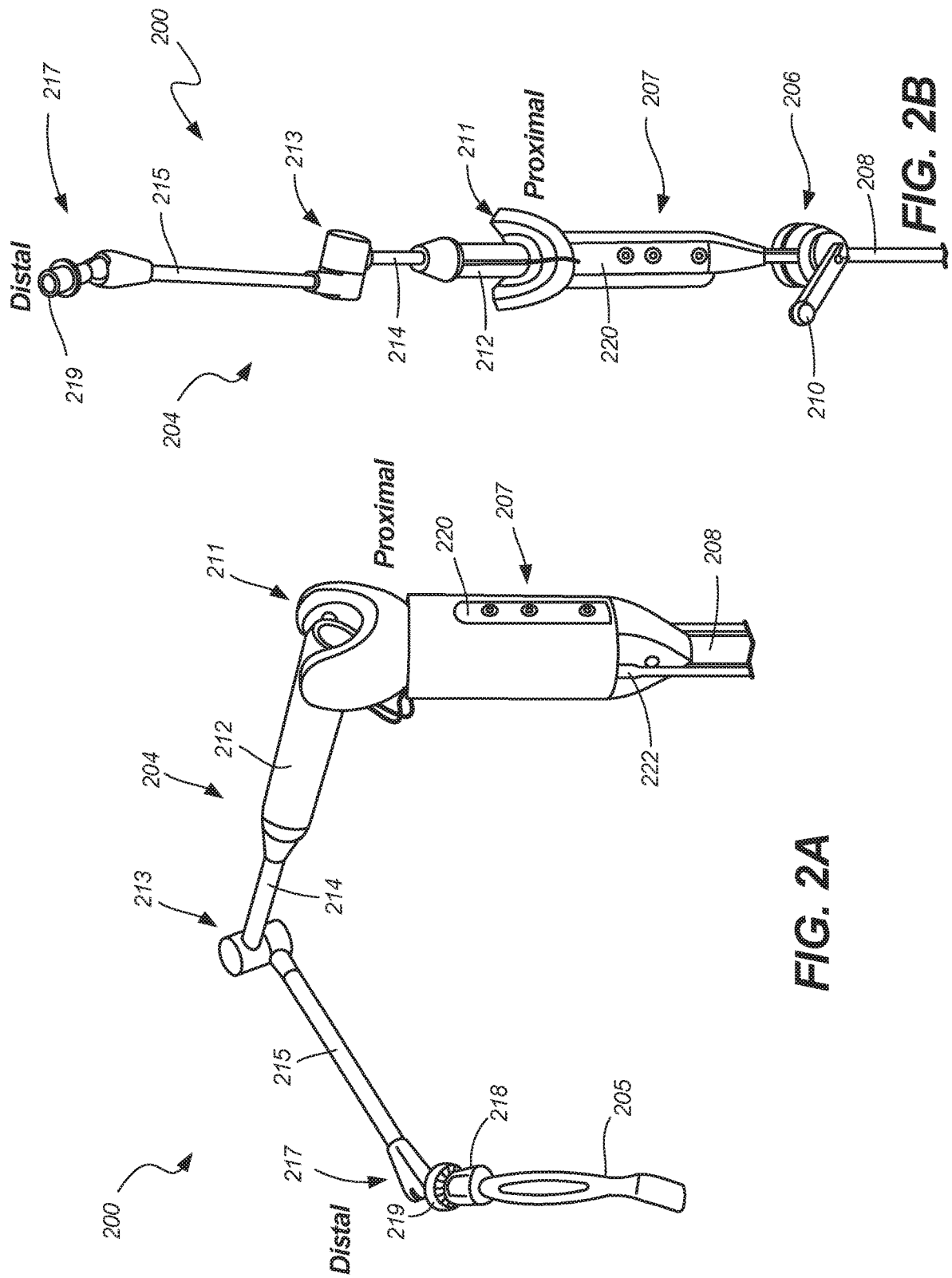
FIG. 2A illustrates a perspective view of a repositionable, lockable surgical arm, in accordance with at least one example of this disclosure.
FIG. 2B illustrates a perspective view of a repositionable, lockable surgical arm, in accordance with at least one example of this disclosure.

Surgical arm 200 can include arm 204, tool (or instrument) 205, base unit 206 (only shown in FIG. 2B), control device 207, pole 208, and manual clamp 210. Arm 204 can include proximal joint 211, actuator unit 212, distal joint 213, proximal arm 214, distal arm 215, coupler joint 217, end effector coupler 218, and arm coupler 219. Control device 207 can include user interface 220 and can be connected to cable 222. Also shown in FIG. 2 are orientation indicators Proximal and Distal.

Surgical arm 200 can be similar to system 100 discussed above, except that surgical arm 200 can include different features. For example, base unit 206 can be a manually adjustable unit, where manual clamp 210 can be operable to adjust a position of base unit 206 along a rail (e.g., surgical table rail) and to adjust the height of pole 208 (and therefore arm 204). In this example, control device 207 can include electronic components configured to control arm 204. For example, control device 207 can house a controller (discussed further below) and user interface 220, which can include one or more control inputs (such as buttons and switches) and can include audible or visual indicia. Cable 222 can be coupleable to control device 207 to connect a lock/unlock button to control device 207.

Surgical arm 200 can also include arm coupler 219 which can be a distal coupler of arm 204 configured to releasably secure end effector coupler 218 to coupler joint 217 (and therefore to arm 204). In other examples, discussed below, end effector coupler 218 can be fixedly secured to arm 204.

Surgical arm 204 can operate consistently with system 100 described above, except that coupler joint 217 can offer additional range of motion of the embodiment shown in FIG. 1. Further, end effector coupler 218 can be used to quickly and easily remove and secure tools and instruments, such as tool 205, to surgical arm 204, as discussed in further detail below.

Figure 3:
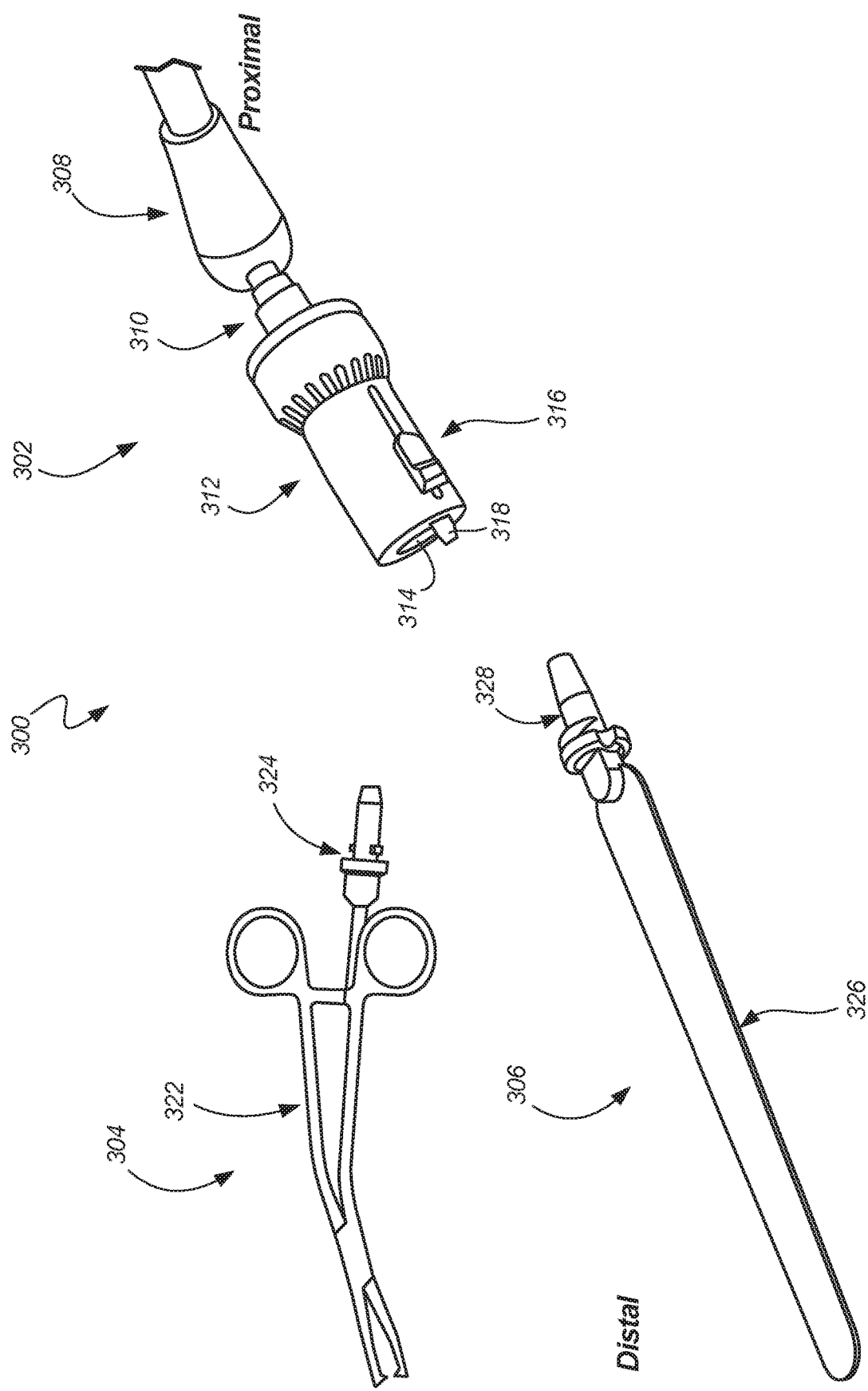
FIG. 3 illustrates a perspective view of a surgical system, in accordance with at least one example of this disclosure.

FIG. 3 illustrates a perspective view of surgical system 300, in accordance with at least one example of this disclosure. End effector system 300 can include arm 302, forceps 304, and retractor 306. Arm 302 can include distal arm 308, arm coupler 310, and end effector coupler 312. End effector coupler 312 can include keyed opening 314, pin release 316, and pin 318. Forceps 304 can include tool portion 322 and stem 324. Retractor 306 can include tool portion 326 and stem 328. Also shown in FIG. 3 are orientation indicators Proximal and Distal.

Arm 302 can be consistent with arms 104 and 204 discussed above, however, arm 302 shows additional detail of end effector 312, which can be releasably coupled to distal arm 308 via distal coupler 310. End effector coupler 312 can be a coupler configured to releasably secure tools and instruments, such as forceps 304 and retractor 306, to arm 302.

Forceps 304 can be surgical forceps including stem 324 extending from tool portion 322. Stem 324 can be coupled to tool portion 322 of forceps 304 such that stem 324 does not interfere with the operation of tool portion 322 of forceps 304. Retractor 306 can be a substantially flat and/or malleable retractor, such as a ribbon retractor, including stem 328 extending from tool portion 326 of retractor 306. Stem 328 can be coupled to tool portion 326 of retractor 306 such that stem 328 does not interfere with the operation of tool portion 326 of retractor 306. Each of stems 324 and 328 can be of identical structure where each can include tapered stems configured and shaped to be inserted into end effector coupler 312 through keyed opening 314, as discussed in further detail below.

Keyed opening 314 of end effector coupler 312 can include an irregular geometric shape that is sized and shaped to receive each of stems 324 and 328 therethrough to individually secure each of stems 324 and 328 within end effector 312. That is, end effector coupler 312 can secure one stem at a time. Pin 318 of end effector can be disposed within a pin bore of end effector and can extend from a distal end of end effector coupler 312 such that pin 318 can engage a tool stem to help secure the tool stem to the end effector coupler 312. Pin 318 can be coupled to pin release 316, where pin release 316 can be operable to translate pin 318.

In operation of some examples, either of stems 324 and 328 can be oriented for insertion into keyed opening 314. Once inserted, the stem can be rotated so that the stem locks into end effector coupler 312 so that a tapered distal end of pin 318 engages an angled (or straight) notch of a collar of the stem to restrict rotation of the stem while within end effector coupler 312. The tool (forceps 304, retractor 306, or other tools, as discussed below) can then be used in a surgical procedure while connected to end effector coupler 312. And, when a lock/unlock button is activated (as discussed in FIGS. 1 and 2 above), end effector coupler 312 and the tool can be positioned as desired (and repositioned) and can be guided by arm 302. Alternatively, the tool can be positioned as desired and then connected to arm 302 when in position.

When the tool is in a desired position, the lock/unlock button can be de-activated (or released) to lock a position of arm 302 and therefore of end effector coupler 312 and the tool (e.g., retractor 306) secured to end effector coupler 312. The tool can then be used in the desired position and repositioned at any time. When it is desired to remove or change tools, pin release 316 can be actuated to retract pin 318 so that the tool (and stem 324 or 328) can be rotated within end effector coupler 312 to allow for removal of the stem and tool out of keyed opening 314 and out of end effector coupler 312. This process can be repeated, such that a new tool can be inserted and removed in the same manner.

Figure 4:
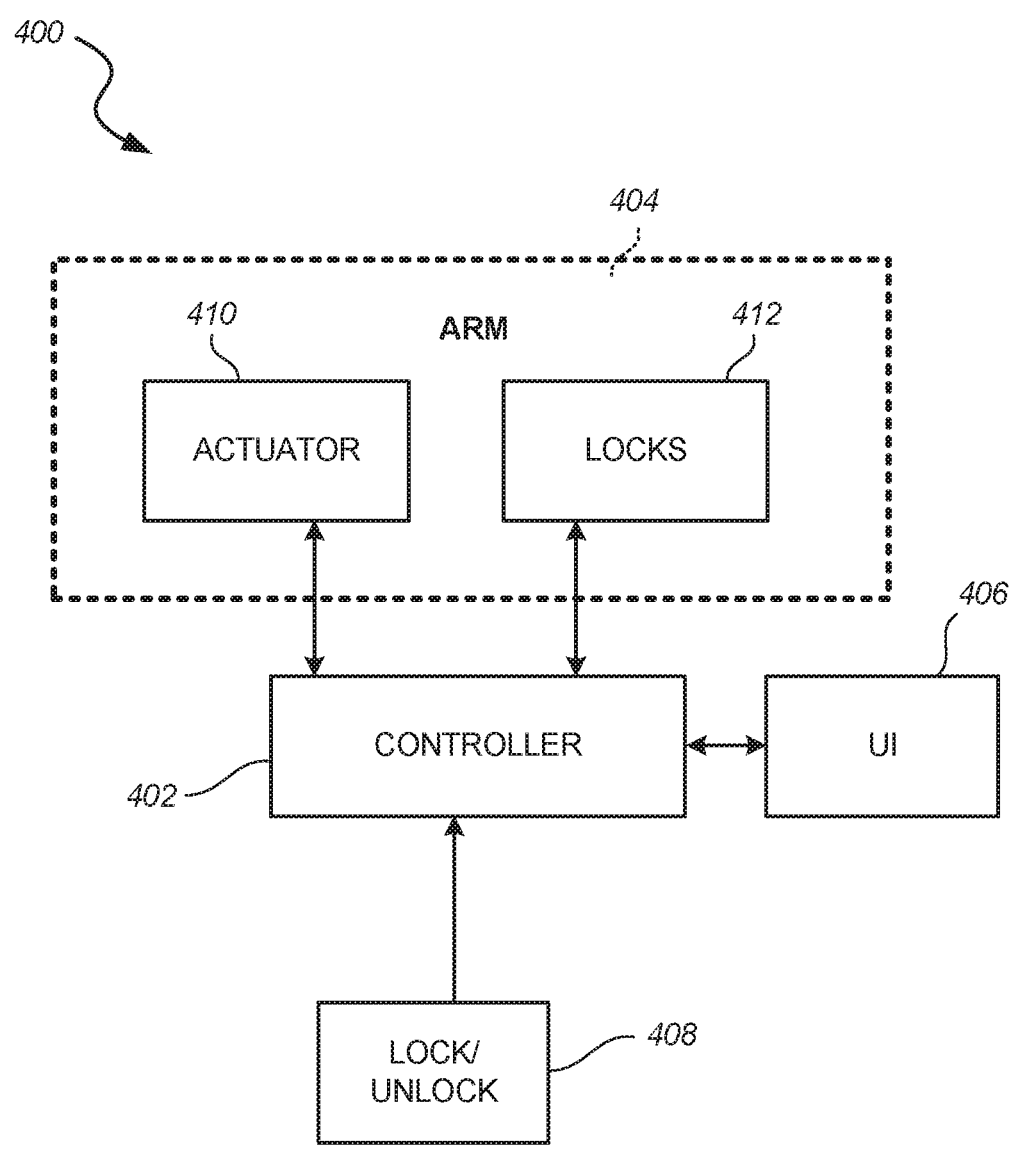
FIG. 4 illustrates a schematic view of a system, in accordance with at least one example of this disclosure.

FIG. 4 illustrates a schematic view of control system 400, in accordance with at least one example of this disclosure. Control system 400 can include controller 402, surgical arm 404, user interface 406, and lock/unlock button 408. Surgical arm 404 can include actuator 410 and lock(s) 412.

Controller 402 can be a programable controller, such as a single or multi-board computer, a direct digital controller (DDC), or a programable logic controller (PLC). In other examples controller 402 can be any computing device, such as a handheld computer, for example, a smart phone, a tablet, a laptop, a desktop computer, or any other computing device including a processor and wireless communication capabilities.

Surgical arm 404 can be similar to the arms discussed above with respect to FIGS. 1-3 in that arm 404 can be a movable arm that is lockable in a desired position. Actuator 410 can be an electric, fluid, or gas powered actuator in communication with controller 402 and can be operable to translate or otherwise move one or more components (such as an armature) in response to a control signal. Actuator 410 can be physically coupled to locks 412 which can be mechanical or electro-mechanical locks coupled to joints or arms of arm 404. In other examples, actuator 410 can be omitted and locks 412 can be individually operable in response to individual or shared control signals from controller 402.

Control system 400 can optionally include user interface 406 that can be in communication with controller 402. In another example, user interface 406 can be separate from control system 404 or can be communicatively coupled to control system 404.

Lock/unlock button 408 can be a simple button or switch in some examples and can be in communication with controller 402. In some examples, button 408 can be attached to a portion of arm 404. In other examples, button 408 can be attached to other components, such as table 102 of FIG. 1 or can be located on a floor and can be operated as a foot pedal or switch. In other examples, a controller may not be present and lock/unlock button 408 can be in direct communication with actuator 410 and/or locks 412.

User interface 406 can be any display and/or input device. For example, user interface can be a monitor, keyboard, and mouse in one example. In other examples, user interface 406 can be a touch screen display. In yet another example, user interface 406 can provide lights, buttons, and/or switches. Controller 402 and user interface 406 can include machine readable medium. The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

In operation of some examples, a user can interact with user interface 406 to power on control system 400. Power can be indicated by a light, for example, on user interface 406 and/or on arm 404. The user can then operate button 408 to send an unlock signal to controller 402 to initiate power locking and unlocking of arm 404. In response, controller 402 can send a signal to actuator 410 and/or locks 412 to unlock locks 412. Once arm 404 is unlocked, the user can move an instrument and arm 404 to a desired location and orientation relative to a patient. When the user releases the lock/unlock button, it can send a lock signal (or can cease sending an unlock signal) to controller 402. In response, controller 402 can send a signal (or can cease sending an unlock signal) to actuator 410 and/or locks 412 to lock the joints of arm 404, locking arm 404 in the desired position such that the joints of arm 404 cannot articulate and the end effector of arm 404 cannot move relative to arm 404.

Though the components of control system 400 are shown as being wired to controller 402, the lines of FIG. 4 connecting components of control system 400 can also represent wireless communication paths where each component can communicate using wireless (electromagnetic signals) through protocols such as WiFi, Bluetooth (Bluetooth LE), Near-Field Communications (NFC), and the like.

FIG. 5A illustrates a perspective view of end effector coupler 500 in a coupled condition, in accordance with at least one example of this disclosure. FIG. 5B illustrates a perspective view of end effector coupler 500 in a decoupled condition, in accordance with at least one example of this disclosure. FIGS. 5A and 5B are discussed below concurrently.

End effector coupler 500 can include body 502, proximal coupler 504, and tool lock 506. Tool lock 506 can include keyed opening 508, pin bore 510, pin 512 (including tapered portion 512*t*), biasing element 514, and pin release 516. Keyed opening 508 can include central bore 518 (or stem opening) and keyways 520*a* and 520*b*. Body 502 can also include slot 522. Also shown in FIGS. 5A and 5B is tool 525, which can include stem 526, tool portion 528, and flange 530. Stem 526 can include tapered portion 532 and projections 534 (or key bits 534). Flange 530 can include notches 536*a* and 536*b*. Also shown in FIGS. 5A and 5B are orientation indicators Proximal and Distal and Axis A.

Body 502 can be a rigid or semi-rigid body comprised of materials such as metals, plastics, foams, elastomers, ceramics, composites, and combinations thereof. Body 502 can include proximal portion 502P and an opposite distal portion 502D including a distal end. Body 502 can be sized and shaped to be handheld and hand-positioned. For example, body 502 can be ergonomically shaped and can include ridges or crenellations to promote ergonomics and grip. Slot 522 of body 502 can be an axially extending slot along a side of body 502 adjacent pin bore 510 and can be sized to allow a portion of pin release 516 to extend through body 502 to couple to pin 512.

Proximal coupler 504 can be a rigid or semi-rigid body comprised of materials such as metals, plastics, foams, elastomers, ceramics, composites, and combinations thereof. Proximal coupler 504 can have a substantially hollow cylindrical geometric shape and can be securable to distal portion 502D of body 502. In some examples, proximal coupler 504 can include a threaded portion configured to secure proximal coupler 504 to a surgical arm.

Tool lock 506 can be comprised of multiple components of end effector coupler 500 and can be configured to secure tool 525 to end effector coupler 500. Keyed opening 508 of tool lock 506 can be a central bore 518 of keyed opening 508 configured to receive a tool stem therein. Central bore 518 can be a longitudinal bore extending into body 502 from the distal end of distal portion 502D of body 502. Central bore can extend into body 502 along axis A, which can be central to keyed opening 508 and central to body 502 in some examples, but can be offset from a central axis of body 502 in other examples. In some examples, central bore 518 can be sized to receive tool stem 526 in a taper-to-taper arrangement, as discussed further below.

Keyways 520*a* and 520*b* can be notches extending radially from central bore 518 and can be sized and shaped to receive key bits 534 of tool 525 when key bits 534 are aligned with keyways 520*a* and 520*b*, but can prevent passage of key bits 534 into or out of keyways 520*a* and 520*b* (therefore preventing stem from being inserted into keyed opening 508 or being removed therefrom) when key bits 534 are not aligned with keyways 520*a* and 520*b*. As discussed further below, each of keyways 520*a* and 520*b* can include a proximal face, where each proximal face is engageable with key bits 534 of tool 525.

Pin bore 510 can be a longitudinal bore extending into body 502 from the distal end of distal portion 502D of body 502. In some examples, pin bore 510 can be adjacent (or proximate or near) central bore 518 and can extend through body 502 substantially parallel to central bore 518 and axis A, but can be not parallel to central bore 518 in other examples.

Pin 512 can be a rigid or semi-rigid body comprised of materials such as metals, plastics, foams, elastomers, ceramics, composites, and combinations thereof. Pin 512 can include tapered portion 512*t* at a distal termination of pin 512. Pin 512 can be disposed within pin bore 510 such that tapered portion 512*t* extends from pin bore 510 (and therefor beyond distal portion 502D of body 502 when pin 512 is in an extended or locked position.

Biasing element 514 can be a resilient element such as a spring. In some examples, biasing element 514 can be a compression coil spring. In other examples, biasing element can be other springs or resilient members, such as a wave spring or compressible and resilient members comprised of materials such as rubbers, plastic, and the like. In some examples, biasing element can be disposed within pin bore 510 to engage a proximal termination of pin bore 510 and to engage a proximal termination of pin 512, such that biasing element 514 biases pin 512 distally relative to body 502. Pin release 516 can be an actuator operable by hand or tool and can be coupled to pin 512 through slot 522 of body 502.

Tool 525 can be a surgical tool such as forceps or a retractor (as described below), or various other surgical tools that can be adapted to include a stem. Stem 526 can be a keyed stem, shaped and sized to be inserted within end effector coupler 500 to secure tool 525 to end effector coupler 500. Tool portion 528 can be connected to the operable tool, such as the forceps or retractor. Flange 530 can be a flange or collar extending radially outward from stem and can include notches 536*a* and 536*b* extending substantially axially therethrough (though notches 536*a* and 536*b* can extend through flange 530 at an axis not parallel with the axis of stem 526, in some examples).

Stem 526 can also include tapered portion 532, which can be sized and shaped to extend into central bore 518 of keyed opening 508, where stem 526 can be tapered to mate with a tapered bore of body 502. Key bits 534 of stem 526 can be projections extending radially outward from stem 526 and key bits 534 can be sized and shaped to pass through keyways 520*a* and 520*b* when key bits 534 are aligned with keyways 520*a* and 520*b*. Key bits 534 can also be used to secure stem 526 within central bore 518 as discussed further below.

In operation of some examples, tool 525 can be separate from end effector coupler 500, as shown in FIG. 5B. When it is desired to secure tool 525 to end effector coupler 500, tool stem 526 can be inserted into central bore 518 and rotated clock-wise approximately one quarter of a turn to secure tool 525 to end effector coupler 500. In other examples, tool 525 (and stem 526) can be rotated greater than a quarter turn, such as a half or three-quarters turn, and can be rotated less than a quarter turn, such as a one-eighth or one-sixteenth turn.

More specifically, tool stem 526 can be inserted into central bore 518 until key bits engage body 502. Key bits 534 can then be aligned with keyways 520a and 520b to allow tool stem 526 to be further inserted into central bore 518. As discussed further below, tool stem 526 can then be rotated clockwise (from a distal perspective) to seat key bits 534 within a counterbore of central bore 518, where contact between key bits 534 and portions of central bore 518 draw tool stem 526 completely into central bore 518 as stem 526 is rotated. In other examples, tool stem 526 can be rotated counter-clockwise to seat key bits 534 within the counterbore of central bore 518.

Alternatively, tool stem 526 can be inserted into central bore 518 until key bits engage body 502. Key bits 534 can then be aligned with keyways 520a and 520b to allow tool stem 526 to be further inserted into central bore 518 entirely until key bits 534 rest within a counter bore of central bore 518 which extends stem 526 entirely into central bore 518. Tool stem 526 can then be rotated clockwise (from a distal perspective) to seat key bits 534 within the counterbore of central bore 518.

During insertion of tool stem 526 into central bore 518, a proximal portion of flange 530 can contact pin 512 to cause pin 512 to move proximally into pin bore 510. As tool stem 526 is rotated, one of notches 536a and 536b will align with tapered portion 512t of pin 512 as key bits 534 draw tapered portion 532 into central bore 518, allowing pin 512 to extend from pin bore 510 and into either notch 536a or notch 536b. Pin 512 can automatically extend to this extended position due to being biased to extend distally from pin bore 510 by biasing element 514. When pin 512 is in this position, pin 512 can apply a force from biasing element 514 on flange 530 to further ensure a stable connection between tool 525 and end effector coupler 500. Also, as pin 512 engages one of notches 536a and 536b, the interaction can produce a noise in addition to being visible through one of notches 536a or 536b, which can provide indications to an operator that tool 525 is secured to end effector coupler 500.

The taper-to taper interface of stem 526 with central bore 518 and the engagement of key bits 534 with a proximal portion of keyed opening 508 and the counterbore of central bore 518 can both help limit undesired movement of tool 525 relative to end effector coupler 502; and, the engagement of flange 530 with pin 512 can help limit counter-clockwise rotation of tool 525 relative to central bore 518 and body 502 to help prevent back-out of tool 525 from end effector coupler 500, securing tool 525 to end effector coupler 502. In some examples, during insertion of stem 526 into central bore 518, contact between taper-to taper interface of stem 526 with central bore 518 can occur substantially simultaneously as the engagement of key bits 534 with a proximal portion of keyed opening 508 and substantially simultaneously as the engagement of flange 530 with pin 512 so that stem 526 is secured in all directions relative to end effector coupler 502 all at once.

Also, because tapered portion 512t is tapered and because notches 536a and 536b can be angled, tapered portion 512t can contact a large surface area of either one of notches 536a and 536b. This contact can further help limit unwanted back-out of tool 525 from end effector coupler 500. All of these features that help secure tool 525 to end effector coupler 500 can provide a wear resistant design for the application where users frequently change instruments for different procedures.

When it is desired to remove tool 525 from end effector coupler 500, pin release 516 can be translated proximally, where slot 522 guides and limits translation of pin release 516. Proximal retraction of pin release 516 can retract pin 512 into pin bore such that pin 510 is no longer engaging a notch (of notches 536a and 536b), as shown in FIG. 6B. This allows a user to rotate tool 525, along with stem 526 and flange 530, counter-clockwise so that key bits 534 can be disengaged from the distal side of keyed opening 508 and can move out of the counterbore and into alignment with keyways 520a and 520b of central bore 518, allowing stem 526 to be removed from central bore 518. Because pin release 516 can be easily actuated by hand and rotation of stem 526 requires about a quarter turn of tool 525 with little resistance, tool 525 can be easily and quickly removed from end effector coupler 500.

FIG. 6A illustrates a top view of end effector coupler 500, in accordance with at least one example of this disclosure. FIG. 6B illustrates a side view of end effector coupler 500, in accordance with at least one example of this disclosure. FIGS. 6A and 6B are discussed below concurrently.

End effector coupler 500 of FIGS. 6A and 6B can be consistent with end effector coupler 500 of FIGS. 5A and 5B; however, FIGS. 6A and 6B show end effector coupler 500 from different perspectives. Also, FIG. 6B shows pin 512 of end effector coupler retracted into pin bore 510 where pin release 516 is translated distally relative to body 502. When pin 512 is in this retracted position, tool 525 can be rotated relative to body 502 because tapered portion 512t of pin 512 is not disposed within notch 536 to restrict rotation of flange 530, thus allowing tool 525 to be rotated relative to body 502.

FIGS. 6A and 6B also show how proximal coupler 504 of end effector coupler 500 can be secured to proximal connector 540 of a surgical arm. In some examples, coupler 504 can be threadably engaged with distal connector 540, as discussed in further detail below.

FIG. 7A illustrates a perspective view of end effector coupler 500, in accordance with at least one example of this disclosure. FIG. 7B illustrates a bottom perspective view of end effector coupler 500, in accordance with at least one example of this disclosure. FIGS. 7A and 7B are discussed below concurrently.

End effector coupler 500 of FIGS. 7A and 7B can be consistent with end effector coupler 500 of FIGS. 5A-6B above; however, FIGS. 7A and 7B show internal bores of end effector coupler 500. For example, FIG. 7A shows pin bore 510 extending longitudinally into body substantially parallel with axis A of keyed opening 508, where pin bore 510 is diametrically sized to retain pin 512 and biasing element 514 (FIG. 7B) therein and can terminate or reduce diameters near proximal end 502D of body 502 to axially retain pin 512 and biasing element 514 in a proximal direction.

FIGS. 7A and 7B also show how central bore 518 and keyways 520a and 520b extend longitudinally (axially parallel with axis A) into body 502. FIGS. 7A and 7B also show counterbore 540 of central bore 518 which can extend radially outward from central bore 518 between central bore taper 544 and keyways 520a and 520b. Central bore taper 544 can be a tapered portion of central bore 518 that is complimentary to tapered portion 532 of stem 526. In some examples, tapered portion 532 and central bore taper 544 can have one consistent taper and in other examples, tapered portion 532 and central bore taper 544 can have multiple tapered portions of varying taper sizes and/or styles including Brown, Morse, Jarno, Jacobs, and the like tapers.

FIG. 7B also shows stem 546 of pin release 516, which can be a protuberance of pin release 516 that connects pin release 516 to pin 512 through slot 522 (shown in FIG. 5B). FIG. 7B additionally shows drainage bores 548 and 550, which can be connected to central bore 518 and pin bore 510, respectively and can be connected to each other. Drainage bores 548 and 550 can allow for fluids and other substances to drain from body 502 after a cleaning process, such as an autoclaving process, helping to make end effector coupler 500 autoclavable. The components of end effector coupler 500 can also be manufactured out of metals, such as stainless steel and titanium, that are autoclavable.

FIG. 7B also shows how projections (or key bits) 534 can be clocked relative to notches 536 of flange 530. Key bits 534 can be circumferentially placed about stem 526 relative to notch 536 so that pin 512 engages a notch 536 as projections 534 engage a proximal portion of where central bore 518 meets counterbore 540. The engagement by projections 534 forces tapered portion 532 to translate proximally to create a taper-to-taper interface between tapered portion 532 of stem 526 and central bore taper 544. This relative positioning of key bits 534 to notches 536 ensures that rotation prevention of stem 526 does not occur until the taper-to-taper interface is made, helping to secure tool 525 to body 502.

Alternatively, in operation of some examples, key bits 534 can be aligned with keyways 520a and 520b to allow tool stem 526 to be inserted entirely into central bore 518 until key bits 534 rest within counter bore 540 so that stem 526 engages central bore 518 in a taper-to-taper engagement. Tool stem 526 can then be rotated clockwise (from a distal perspective) so that key bits 534 engage a proximal face of keyways 520a and 520b to seat key bits 534 within counterbore 540 of central bore 518.

Figure 8B:
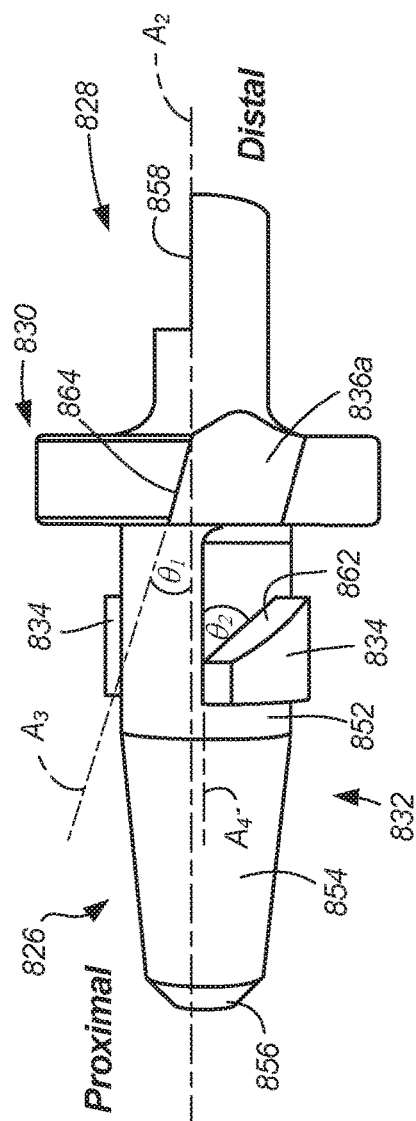
FIG. 8B illustrates a side view of a tool securable to an end effector coupler, in accordance with at least one example of this disclosure.
Figure 8C:
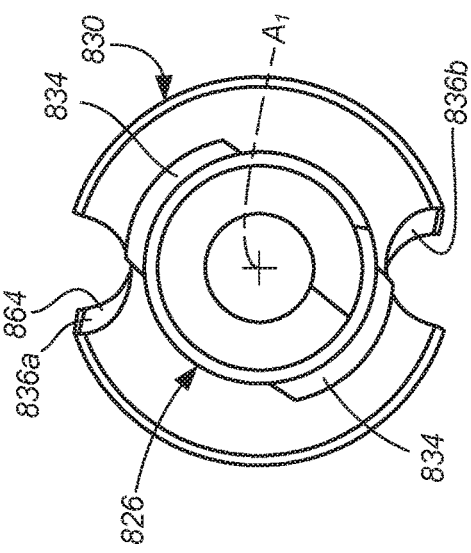
FIG. 8C illustrates an end view of a tool securable to an end effector coupler, in accordance with at least one example of this disclosure.
Figure 8A:
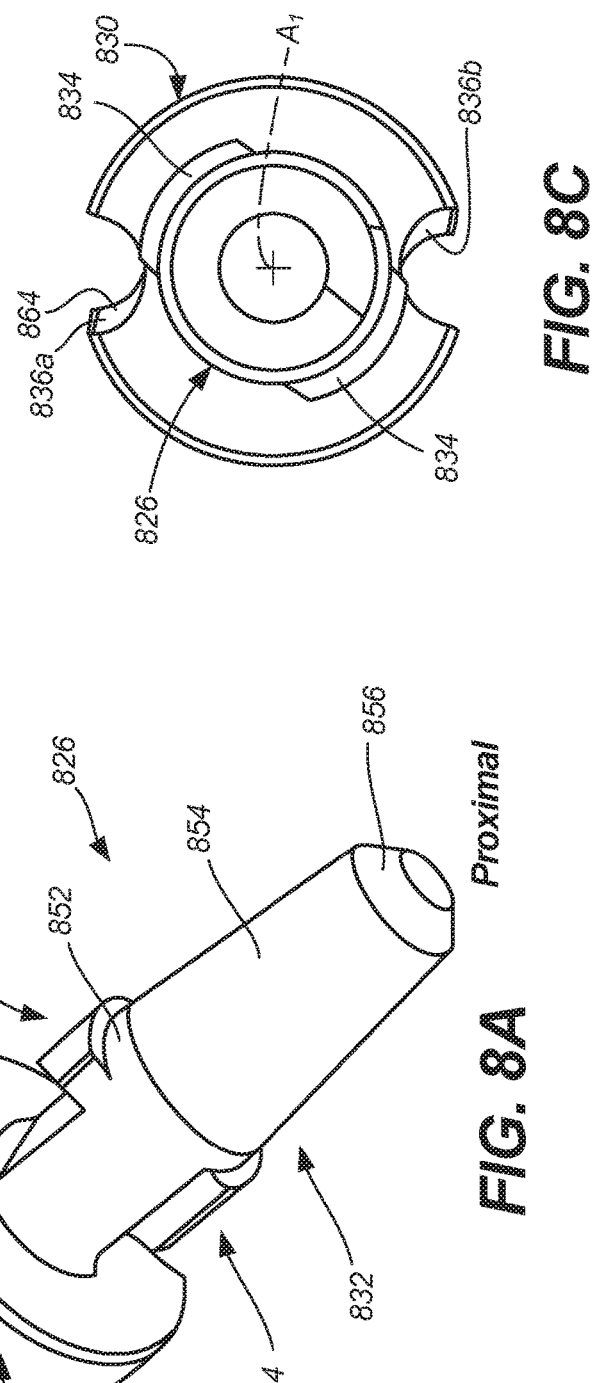
FIG. 8A illustrates a perspective view of a tool securable to an end effector coupler, in accordance with at least one example of this disclosure.

FIG. 8A illustrates a perspective view of tool 825 securable to an end effector coupler, in accordance with at least one example of this disclosure. FIG. 8B illustrates a side view of tool 825 securable to an end effector coupler, in accordance with at least one example of this disclosure. FIG. 8C illustrates an end view of tool 825 securable to an end effector coupler, in accordance with at least one example of this disclosure. FIGS. 8A-8C are discussed concurrently below.

Tool 825 can include stem 826, tool portion 828, and flange 830. Stem 826 can include stem taper 832 and projections 834 (or key bits 834). Flange 830 can include notches 836a and 836b (associated with angle θ1). Stem taper 832 can include first stem taper 852, second stem taper 854, and third stem taper 856. Tool portion 828 can include tool connection flat 858. Key bits 834 can each include angled face 862 (associated with angle θ2) (FIG. 5B). Also shown in FIGS. 8A and 8B are orientation indicators Proximal and Distal and Axes A1, A2, A3, and A4.

Tool 825 can be similar to tool 525 discussed above, but FIGS. 8A-8C show further detail of tool 825, as discussed below. For example, FIGS. 8A and 8B show how stem taper 832 can include three tapered portions: first stem taper 852, second stem taper 854, and third stem taper 856. In some examples, each tapered portion can have a different taper size and/or taper style including Brown, Morse, Jarno, Jacobs, and the like tapers. In some examples, some of first stem taper 852, second stem taper 854, and third stem taper 856 may be straight (or not tapered). For example, first stem taper 852 may be of a constant diameter along its axial length.

FIGS. 8A-8C also shows how key bits 834 can be radially extending protuberances of stem 826, which can have a substantially trapezoidial geometric shape from a top perspective, with angled face 862 facing distally (toward flange 830). However, key bits 834 can have other shapes in other examples. Angled face 862 can be provided at angle θ2, where angle θ2 (between angled face 862 and axis A4) is selected to cause notch 836 to align with a pin of an end effector coupler when stem 826 is fully seated within a tapered bore of the end effector coupler, as caused by engagement of face 862 with a proximal portion of a keyed opening of the end effector. Axis A4 can be coaxial and/or parallel with axis A of FIG. 5B. Also, because angled face 836 is angled in a single direction, it ensures that tool 825 is rotated in the proper (clockwise) direction, as rotation in the opposite (counter-clockwise) direction will be prevented by contact with a non-angled face of key bit 834 and a keyway and/or counterbore of the keyed opening of the end effector coupler.

FIGS. 8B and 8C also shows axes A1 and A2, where axis A1 can be a central longitudinal axis of stem 826 (which may or may not be coaxial and/or parallel with axis A of FIGS. 5A and 5B) and axis A2 can be parallel with axis A1 but spaced away therefrom. Axis A3 can be parallel with edge 864 of notch 836a. That is, notches 836a and 836b can be formed at an angle relative to axes A1 and A2. FIG. 8B shows θ1 between edge 864 (along axis A3) and axis A2. Angle θ1 of notches 836a and 836b can be selected to be complementary with a taper of a tapered distal tip of the pin (such as tapered portion 512t discussed above), which can provide a large contact surface area between a pin and flange 830 to limit play between the end effector and tool 825.

Tool portion 828 can include tool connection flat 858, which can be a substantially planar surface of tool portion 828 for manufacturing purposes. For example, tool 825 can be manufactured using machining processes (such as a lathe, etc.), and can then be attached (via welding or other fastening means) to a tool that is manufactured in separate processes. This can be helpful when the tool is not manufacturable through the same processing steps as tool 825, such as when tool 825 connects to forceps (such as forceps 304 of FIG. 3).

Figure 9A:
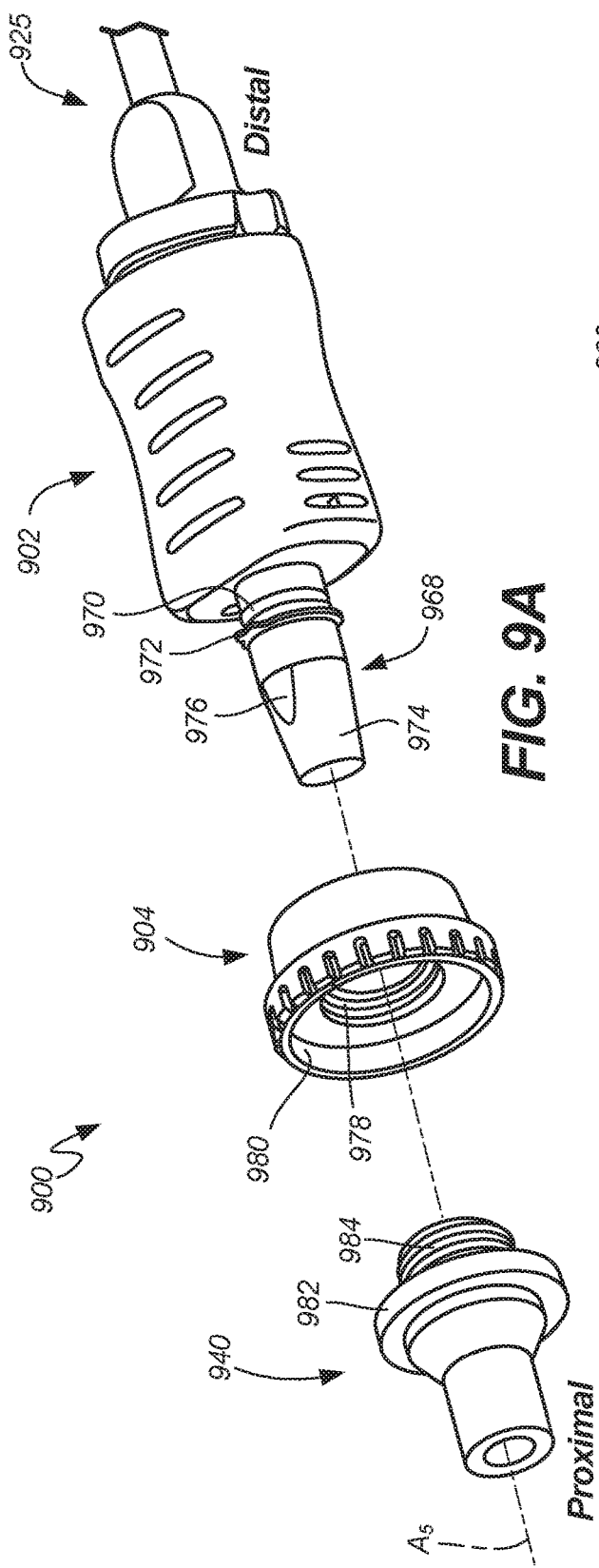
FIG. 9A illustrates a partially exploded view of an end effector coupler from a distal perspective in a first condition, in accordance with at least one example of this disclosure.
Figure 9B:
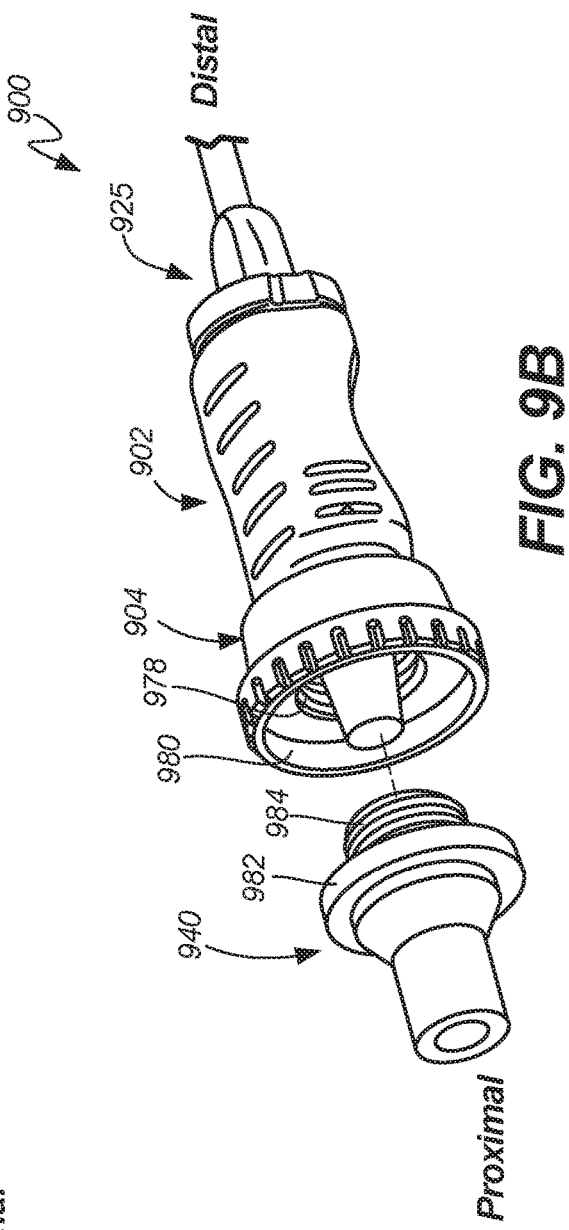
FIG. 9B illustrates a partially exploded view of an end effector coupler from a distal perspective in a second condition, in accordance with at least one example of this disclosure.
Figure 9C:
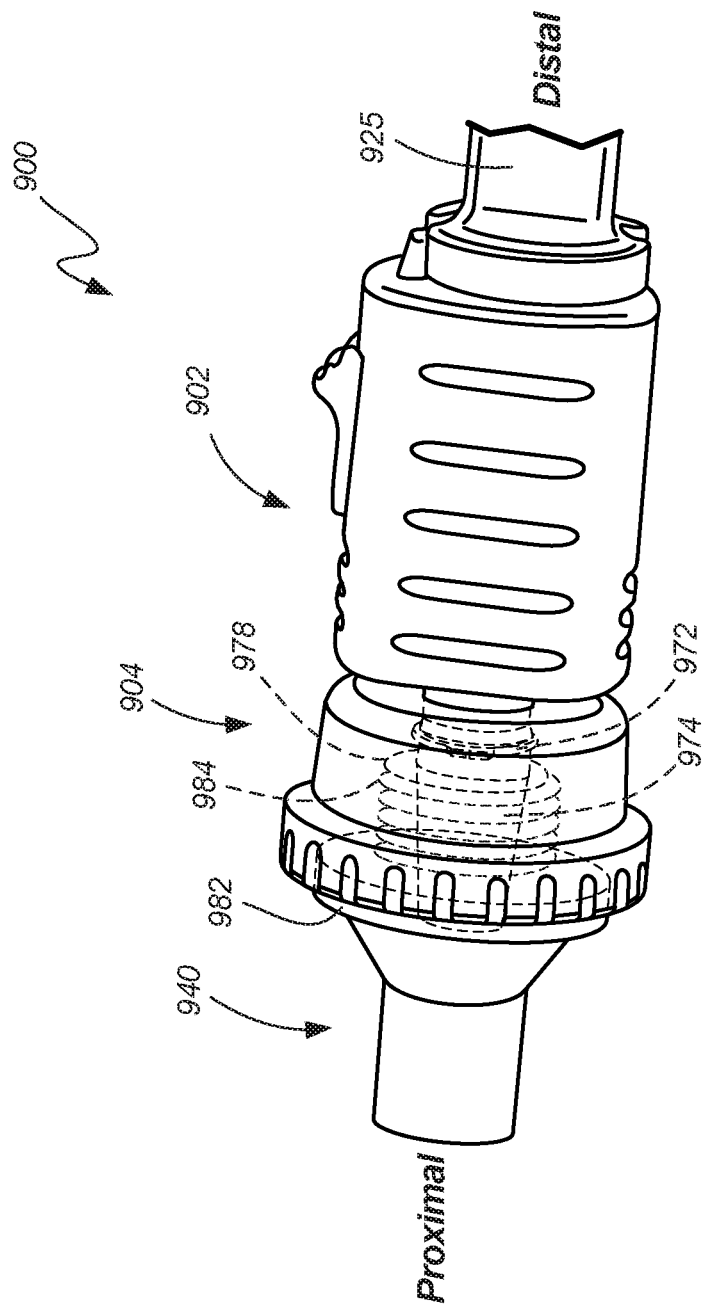
FIG. 9C illustrates a perspective view of an end effector coupler in a third condition, in accordance with at least one example of this disclosure.

FIG. 9A illustrates a partially exploded view of end effector 900 coupler from a distal perspective in a first condition, in accordance with at least one example of this disclosure. FIG. 9B illustrates a partially exploded view of end effector coupler 900 from a distal perspective in a first condition, in accordance with at least one example of this disclosure. FIG. 9C illustrates a perspective view of end effector coupler 900 in an assembled condition, in accordance with at least one example of this disclosure. FIGS. 9A-9C are discussed below concurrently.

End effector coupler 900 can include body 902, proximal coupler 904, distal connector 940 of a surgical arm, and tool 925. Body 902 can include protrusion 968, which can include groove 970, ring 972, taper 974, and flat 976. Proximal coupler 904 can include threaded portion 978, and counter bore 980. Distal connector 940 can include flange 982 and threaded insert 984. Also shown in FIGS. 9A and 9B are axis A5 and orientation indicators Proximal and Distal.

FIG. 9A shows body 902 separated from collar 940 and separated from distal connector 940, where all three components are substantially in axial alignment about axis A5. Body 902 can be consistent with body 502, for example, but FIGS. 9A and 9B show protrusion 968 extending proximally from a proximal portion of body 902.

Protrusion 968 includes groove 970, which can be a circumferential groove around protrusion 968 between body 902 and taper 974. Groove 970 can be sized to retain collar 904 and/or ring 972 (which can retain collar 904). Ring 972 can be a retaining ring, such as a snap ring or retainer, in some examples, where ring 972 can be sized to be disposed in groove 970 and can be selected to retain or captivate collar 904 on protrusion 968.

Taper 974 can be a tapered portion of protrusion 968 and can have multiple tapered portions of varying taper sizes and/or styles including Brown, Morse, Jarno, Jacobs, and the like tapers. Taper 974 can be shaped complementary to a tapered bore of distal connector 940, as discussed below in FIG. 11. Also, taper portion 974 can include flat 976, which can be a substantially planar surface of taper 974 configured for alignment of end effector coupler 902 and distal connector 940 as well as to prevent rotation of end effector coupler 902 to distal connector 940, as discussed in FIG. 11 below. In some examples, there can be two or more of flat 976 of taper portion 974. When two of flat 976 are included, flats 976 can be located on opposite sides of taper portion 974.

Proximal coupler 904 can include threaded portion 978, which can be a female threaded portion configured to receive threaded insert 984 of distal connector 940. Counter bore 980 of proximal coupler 904 can be sized and shaped to receive and retain flange 982 of distal connector 940 therein, in some examples, where flange 982 is a radial extension from distal connector 940 positioned at a proximal termination of threaded insert 984. Threaded insert 984 can be a male threaded portion configured to threadably engage threaded portion 978.

In assembly of some examples, collar 904 can be placed on protrusion 968 proximate body 902. Ring 972 can then be secured to protrusion at groove 970 to retain collar 904 between ring 972 and body 902 such that collar 904 is secured to body 902, as shown in FIG. 9B. However, ring 972 does not firmly engage coupler 904 against body 902, allowing proximal coupler 904 to spin or rotate independent of body 902.

Then, as shown in FIG. 9C, taper 974 can be inserted into distal connector 940 and threaded insert 984 can be inserted into threaded portion 978 of proximal coupler 904. Proximal coupler 904 can then be rotated to threadably secure threaded insert 984 to threaded portion 978, thereby securing body 902 to distal connector 940. During threading of proximal coupler 904 to distal connector 940, proximal coupler contacts a distal side of ring 972 to draw body 902 proximally toward distal connector 940. Following a procedure, this process can be reversed to remove end effector coupler 902 for cleaning (autoclaving) allowing end effector coupler 900 to be reusable.

Figure 10:
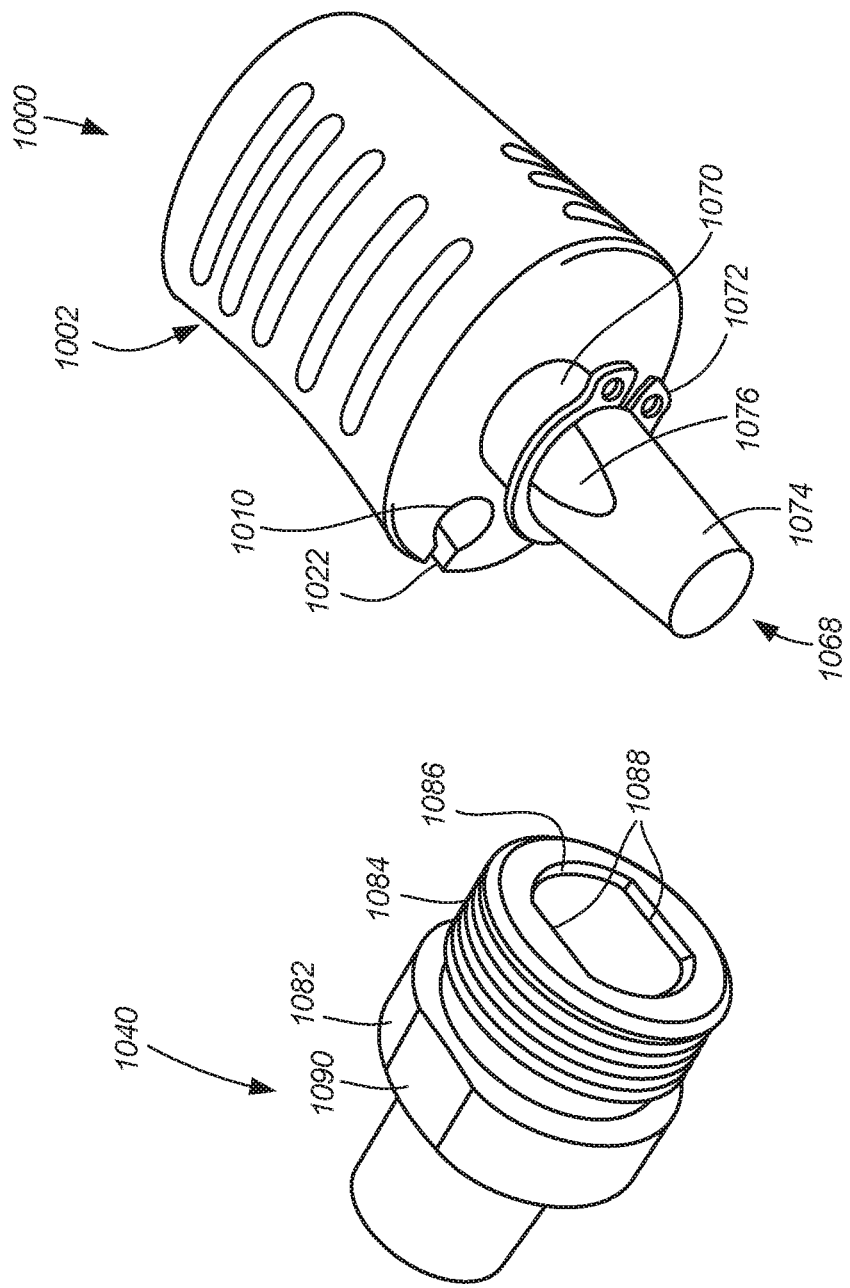
FIG. 10 illustrates a perspective view of components of an end effector, in accordance with at least one example of this disclosure.

FIG. 10 illustrates a perspective view of distal connector 1040 and end effector coupler 1000 with the coupler removed, in accordance with at least one example of this disclosure. End effector coupler 1000 can include body 1002 and protrusion 1068. Body 1002 can include pin bore 1010 and slot 1022. Protrustion can include groove 1070, ring 1072, taper 1074, and flat 1076. Distal connector 1040 can include flange 1082 (which can include flat 1090), threaded insert 1084, and protrusion tapered bore 1086 (which can include flat 1088).

End effector coupler 1000 and distal connector 1040 can be similar to those discussed above (for example, end effector coupler 900 and distal connector 940); however, FIG. 10 further illustrates details of end effector coupler 1000 and distal connector 1040. For example, FIG. 10 shows how pin bore 1010 and slot 1022 can extend through a proximal end of body 1002, which can simplify assembly of end effector coupler 1000, and can help make end effector coupler 1000 autoclavable. In this configuration, the coupler (such as proximal coupler 904) can retain the biasing element and pin.

FIG. 10 also shows protrusion tapered bore 1086 including flat 1088. Protrusion tapered bore 1086 can be tapered complementarily to taper 1074 of protrusion 1068 to provide a taper-to-taper connection between end effector coupler 1000 and distal connector 1040 (and therefore between end effector coupler 1000 and a surgical arm), helping to prevented unwanted movement of end effector coupler 1000 and the surgical arm. FIG. 10 also shows flat 1088 of tapered bore 1086 and flat 1076 of protrusion 1068. These flats can be used to quickly align end effector coupler 1000 relative to distal connector 1040 and the surgical arm during attachment of end effector coupler 1000. These flats can also prevent rotation of end effector coupler 1000 relative to distal connector 1040 and the surgical arm during attachment or movement of end effector coupler 1000. Though two flats 1088 are shown in FIG. 10, more or fewer flats, such as 1, 3, 4, 5, 6, and the like, can be used.

FIG. 10 also shows flat 1090 of flange 1082 which can be used to couple to a tool, such as a wrench for retaining distal connector 1040 during connection of distal connector 1040 to end effector coupler 1000.

EXAMPLES

The following, non-limiting examples, detail certain aspects of the present subject matter to solve the challenges and provide the benefits discussed herein, among others.

Example 1 is an end effector coupler for a surgical arm, the end effector coupler comprising: a body comprising a proximal portion and an opposite distal portion, the distal portion including a distal end; a proximal coupler connected to the proximal portion and releasably couplable to the surgical arm; a tool lock for releasably retaining a tool stem to the end effector coupler, the tool lock comprising: a keyed opening extending through the distal end proximally into the distal portion, the keyed opening configured to receive the tool stem therein; a pin bore extending through the distal end proximate to the keyed opening; a pin disposed in the pin bore and extendable from the pin bore to engage and retain the tool stem when the tool stem is inserted into the keyed opening; and a biasing element located in the pin bore and engaging the pin to bias the pin to extend from the distal end; and a pin release comprising an actuator extending beyond an external surface of the body and engaging the pin, the pin release operable to retract the pin into to the body to disengage the pin from the tool stem allowing release of the tool stem from the keyed opening.

In Example 2, the subject matter of Example 1 optionally includes wherein the pin limits rotation of the stem relative to the keyed opening to prevent release of the stem from the keyed opening when the pin engages the stem.

In Example 3, the subject matter of any one or more of Examples 1-2 optionally include wherein the body includes a tapered bore aligned along a central axis running through the keyed opening and configured to receive the tool stem therein.

In Example 4, the subject matter of any one or more of Examples 2-3 optionally include wherein the tapered bore is configured to receive a complimentary tapered section of the tool stem to form a taper-to-taper interface to limit relative motion between the end effector coupler and the tool stem.

In Example 5, the subject matter of any one or more of Examples 1-4 optionally include wherein the proximal coupler further includes a tapered protrusion coaxial with the proximal coupler and extending and engageable with a complimentary tapered bore of a distal portion of the surgical arm to form a taper-to-taper interface to limit relative motion between the surgical arm and the end effector coupler.

In Example 6, the subject matter of Example 5 optionally includes wherein tapered protrusion includes a flat outer surface engageable with a flat surface of the complimentary tapered bore to align the effector relative to the arm.

In Example 7, the subject matter of any one or more of Examples 1-6 optionally include wherein the keyed opening further comprises a keyway extending radially from a central bore of the keyed opening and sized to receive a key bit of the stem therethrough, the key bit including an angled face engageable with a proximal portion of the keyway to limit axial movement of the stem relative to the keyed opening, and wherein the tapered bore is configured to receive a complimentary tapered section of the tool stem to form a taper-to-taper interface to limit relative motion between the end effector coupler and the tool stem, wherein a distal portion of the pin is configured to engage a notch of the tool stem to limit rotation of the tool stem relative to the end effector coupler, and wherein the angled face is configured to engage the proximal portion of the keyway substantially simultaneously with the tapered bore in receipt of the complimentary tapered section of the tool stem and substantially simultaneously with the distal portion of the pin in engagement with a notch of the tool stem.

Example 8 is an assisted surgical system comprising: a surgical arm moveable and lockable in a position selected by a user; a tool movable with the surgical arm, the tool including a stem for coupling the tool to the surgical arm; an end effector coupler comprising: a body including a proximal portion and an opposite distal portion, the distal portion including a distal end; a proximal coupler connected to the proximal portion and releasably couplable to the surgical arm; a tool lock for releasably retaining the tool stem to the end effector coupler, the tool lock comprising: a keyed opening extending through the distal end into the distal portion, the keyed opening configured to receive the tool stem therein; a pin disposed in a pin bore adjacent the keyed opening, the pin extendable from the pin bore to engage and retain the tool stem when the tool stem is inserted into the keyed opening; a biasing element in the pin bore and engaging the pin to bias the pin to extend from the distal end; and a pin release comprising an actuator extending beyond an external surface of the body and engaging the pin, the pin release operable to retract the pin into to the body to disengage the pin from the tool stem allowing release of the tool stem from the keyed opening.

In Example 9, the subject matter of Example 8 optionally includes wherein the pin limits rotation of the stem relative to the keyed opening to prevent release of the stem from the keyed opening when the pin engages the stem.

In Example 10, the subject matter of any one or more of Examples 8-9 optionally include wherein the end effector coupler further includes a tapered bore aligned along a central axis running through the keyed opening and configured to receive the tool stem therein.

In Example 1, the subject matter of Example 10 optionally includes wherein the tapered bore is configured to receive a complimentary tapered section of the tool stem to form a taper-to-taper interface to limit relative motion between the end effector coupler and the tool stem.

In Example 12, the subject matter of any one or more of Examples 8-11 optionally include wherein the proximal coupler further includes a tapered cylindrical protrusion coaxial with the proximal coupler and extending and engageable with a complimentary tapered bore of a distal end of the surgical arm to form a taper-to-taper interface to limit relative motion between the surgical arm and the end effector coupler.

In Example 13, the subject matter of Example 12 optionally includes wherein tapered cylindrical protrusion includes a flat outer surface engageable with a flat surface of the complimentary tapered bore to align the effector relative to the arm.

In Example 14, the subject matter of any one or more of Examples 8-13 optionally include a control device in communication with the surgical arm and operable to transmit a signal to unlock the surgical arm.

In Example 15, the subject matter of any one or more of Examples 8-14 optionally include the stem comprising: a key bit extending radially from the stem, wherein the keyed opening includes a stem opening and a keyway, the stem opening configured to receive the stem therein, and the keyway extending radially from less than a full circumference of the stem opening, the keyway sized to receive the key bit therethrough to allow the effector to receive the stem.

In Example 16, the subject matter of Example 15 optionally includes the key bit further comprising: an angled face on a proximal side of the key bit.

In Example 17, the subject matter of Example 16 optionally includes the keyed opening further comprising: a counterbore extending radially from the stem opening, the counterbore sized to receive the key bit therein to limit axial movement of the stem relative to the keyed opening.

In Example 18, the subject matter of Example 17 optionally includes wherein the angled face of the key bit is configured to engage a distal portion of the keyed opening to draw the stem into the keyed opening when the stem is rotated within the keyed opening.

In Example 19, the subject matter of any one or more of Examples 8-18 optionally include the tool further comprising: a flange extending radially outward from the stem and engageable with the pin to translate the pin distally.

In Example 20, the subject matter of Example 19 optionally includes the flange of the tool further comprising: a notch sized to receive a distal tip of the pin to limit rotation of the tool relative to the end effector coupler when the pin is received within the notch.

In Example 21, the subject matter of Example 20 optionally includes wherein the notch extends through a radially outer portion of the flange and includes an axis not parallel to an axis of the flange to promote contact between the flange and the pin to limit rotation of the tool relative to the end effector coupler when the pin engages the notch.

In Example 22, the system, device, or method of any one of or any combination of Examples 1-21 is optionally configured such that all elements or options recited are available to use or select from.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An end effector coupler for a surgical arm, the end effector coupler comprising:
   a body comprising a proximal portion and an opposite distal portion, the body defining an opening extending through a distal end of the body into the distal portion and defining a tapered bore extending proximally into the body from the opening, the opening and the tapered bore configured to receive a tool stem therein;
   a proximal coupler connected to the proximal portion and releasably couplable to the surgical arm; and
   a tool lock for releasably retaining the tool stem within the tapered bore.

2. The end effector coupler of claim 1, wherein the tapered bore is aligned along an axis running through the opening.

3. The end effector coupler of claim 1, wherein the tapered bore is configured to receive a complimentary tapered section of the tool stem to form a taper-to-taper interface between the end effector coupler and the tool stem.

4. The end effector coupler of claim 1, wherein the tool lock includes:
   a pin bore extending through the distal end proximate to the opening; and
   a pin located in the pin bore and extendable from the pin bore to engage and retain the tool stem when the tool stem is inserted into the opening.

5. The end effector coupler of claim 4, wherein the tool lock includes:
   a biasing element located in the pin bore and engaging the pin to bias the pin to extend from the distal end.

6. The end effector coupler of claim 1, wherein the opening is a keyed. opening.

7. The end effector coupler of claim 6, wherein the keyed opening includes a keyway extending radially from the tapered bore of the keyed opening, the keyway sized to receive a key bit of the tool stem therethrough.

8. A surgical system for use with a surgical arm, the system comprising:
   a tool stem for coupling a tool to the surgical arm; and
   an end effector coupler comprising:
      a body including a proximal portion and an opposite distal portion, the body defining an opening extending through a distal end of the body into the distal portion and defining a tapered bore extending proximally into the body from the opening, the opening and the tapered bore configured to receive the tool stem therein;
      a proximal coupler connected to the proximal portion and releasably couplable to the surgical arm; and
      a tool lock for releasably retaining the tool stem within the tapered bore.

9. The surgical system of claim 8, wherein the tapered bore is aligned along an axis running through the opening.

10. The surgical system of claim 8, wherein the tool stem includes a tapered portion insertable into the bore.

11. The surgical system of claim 10, wherein the tapered bore is tapered complementary to the tapered portion and is configured to receive the tapered portion of the tool stem to form a taper-to-taper interface between the end effector coupler and the tool stem.

12. The surgical system of claim 11, wherein the tapered portion of the tool stem includes a first portion, a second portion, and a third portion.

13. The surgical system of claim 12, wherein the first portion, the second portion, and the third portion each have different taper sizes or different taper types.

14. The surgical system of claim 12, wherein the first portion has a constant diameter and is connected to the second portion, wherein the second portion is tapered and is connected to the third portion, and wherein the third portion is tapered and has a different taper size than the second portion.

15. The surgical system of claim 8, wherein the proximal coupler further includes a tapered protrusion coaxial with the proximal coupler and extending and engageable with a complimentary tapered bore of a distal portion of the surgical arm to form a taper-to-taper interface between the proximal coupler and the surgical arm.

16. The surgical system of claim 15, wherein the tapered protrusion includes a fiat outer surface engageable with a fiat surface of the complimentary tapered bore to align the end effector coupler relative to the surgical arm.

17. An surgical system for use with a surgical arm, the system comprising:
   a tool stem for coupling a tool to the surgical arm, the tool stem including a tapered portion; and
   an end effector coupler comprising:
      a body including a proximal portion and an opposite distal portion, the body defining a keyed opening in a distal end and defining a tapered bore extending proximally into the body from the keyed opening, the keyed opening and the tapered bore configured to receive at least the tapered portion of the tool stem therein;
a proximal coupler connected to the proximal portion and releasably couplable to the surgical arm; and
a tool lock for releasably retaining the tool stem within the tapered bore.

18. The surgical system of claim 17, wherein the tapered bore is tapered complementary to the tapered portion and is configured to receive the tapered portion of the tool stem to form a taper-to-taper interface between the end effector coupler and the tool stem.

19. The surgical system of claim 17, wherein the tapered portion of the tool stem includes a first portion, a second portion, and a third portion.

20. The surgical system of claim 19, wherein the first portion has a constant diameter and is connected to the second portion, wherein the second portion is tapered and is connected to the third portion, and wherein the third portion is tapered and has a different taper size than a taper size of the second portion.

\* \* \* \* \*

UNITED STATES PATENT AND TRADEMARK OFFICE
CERTIFICATE OF CORRECTION

PATENT NO. : 11,389,142 B2
APPLICATION NO. : 16/879500
DATED : July 19, 2022
INVENTOR(S) : Garcia et al.

Page 1 of 1

It is certified that error appears in the above-identified patent and that said Letters Patent is hereby corrected as shown below:

On the Title Page

Item (56), in Column 2, under "Foreign Patent Documents", Line 2, delete "10201510481" and insert --102015104810-- therefor On page 2, in Column 1, under "U.S. Patent Documents", Line 48, delete "2017/0034021" and insert --2017/0340210-- therefor On page 4, in Column 2, under "Other Publications", Line 19, delete "29/721,682," and insert --17/218,455,-- therefor In the Claims In Column 18, Line 9, in Claim 6, delete "keyed." and insert --keyed-- therefor In Column 18, Line 13, in Claim 7, delete "stern" and insert --stem-- therefor In Column 18, Line 57 (First Occurrence), in Claim 16, delete "fiat" and insert --flat-- therefor In Column 18, Line 57 (Second Occurrence), in Claim 16, delete "fiat" and insert --flat-- therefor Signed and Sealed this
Twenty-fourth Day of September, 2024

Katherine Kelly Vidal
*Director of the United States Patent and Trademark Office*